(12) United States Patent
Parker et al.

(10) Patent No.: US 9,934,930 B2
(45) Date of Patent: Apr. 3, 2018

(54) HIGH ASPECT RATIO X-RAY TARGETS AND USES OF SAME

(71) Applicant: FEI Company, Hillsboro, OR (US)

(72) Inventors: N. William Parker, Hillsboro, OR (US); Mark W. Utlaut, Scappoose, OR (US); Laurens Franz Taemsz Kwakman, St. Ismier (FR); Thomas G. Miller, Portland, OR (US)

(73) Assignee: FEI Company, Hillsboro, OR (US)

( * ) Notice: Subject to any disclaimer, the term of this patent is extended or adjusted under 35 U.S.C. 154(b) by 445 days.

(21) Appl. No.: 14/645,689

(22) Filed: Mar. 12, 2015

(65) Prior Publication Data
US 2015/0303021 A1 Oct. 22, 2015

Related U.S. Application Data

(60) Provisional application No. 61/981,330, filed on Apr. 18, 2014.

(51) Int. Cl.
| | |
|---|---|
| *H01J 35/08* | (2006.01) |
| *G01N 23/04* | (2018.01) |
| *G21K 7/00* | (2006.01) |
| *H01J 35/14* | (2006.01) |

(52) U.S. Cl.
CPC ............ *H01J 35/08* (2013.01); *G01N 23/046* (2013.01); *G21K 7/00* (2013.01); *G01N 2223/204* (2013.01); *G01N 2223/419* (2013.01); *H01J 35/14* (2013.01); *H01J 2235/081* (2013.01); *H01J 2235/086* (2013.01)

(58) Field of Classification Search
None
See application file for complete search history.

(56) References Cited

U.S. PATENT DOCUMENTS

| | | | | |
|---|---|---|---|---|
| 2003/0202634 A1* | 10/2003 | Gerchberg | ............. | G02B 27/46 378/147 |
| 2005/0117701 A1* | 6/2005 | Nelson | ................. | G01N 23/203 378/87 |
| 2008/0095298 A1* | 4/2008 | Shefsky | ................. | G01N 23/02 378/2 |

FOREIGN PATENT DOCUMENTS

WO 2015034791 3/2015

OTHER PUBLICATIONS

Alexander Sasov et al., "New type of x-ray source for lensless laboratory nano-CT with 50nm resolution," Developments in X-Ray Tomography VII, Proc. of SPIE vol. 7804, 2010, pp. 8.

(Continued)

*Primary Examiner* — Hoon Song
(74) *Attorney, Agent, or Firm* — Scheinberg & Associates, P.C.; Michael O. Scheinberg; John E. Hillert

(57) ABSTRACT

An x-ray target, a method of using the x-ray target, and a computer program product with instructions for carrying out a method of using the x-ray target. The x-ray target includes a substrate made from a soft x-ray producing material and a high aspect ratio structure made from a hard x-ray producing material. The hard x-ray producing material is embedded in the substrate, formed on the substrate, cantilevered out from the edge of the substrate, or any combination thereof. The high aspect ratio structure comprises a plurality of high aspect ratio structures arranged in one or more grids or arrays, and the high aspect ratio structures in one of the one or more grids or arrays are arranged to form a Hadamard matrix structure.

11 Claims, 15 Drawing Sheets

(56) References Cited

OTHER PUBLICATIONS

J. Cazaux et al., "Recent developments in X-ray projection microscopy and X-ray microtomography applied to materials science," Journal de Physique IV, 1993, vol. 03 pp. 2099-2104.

* cited by examiner

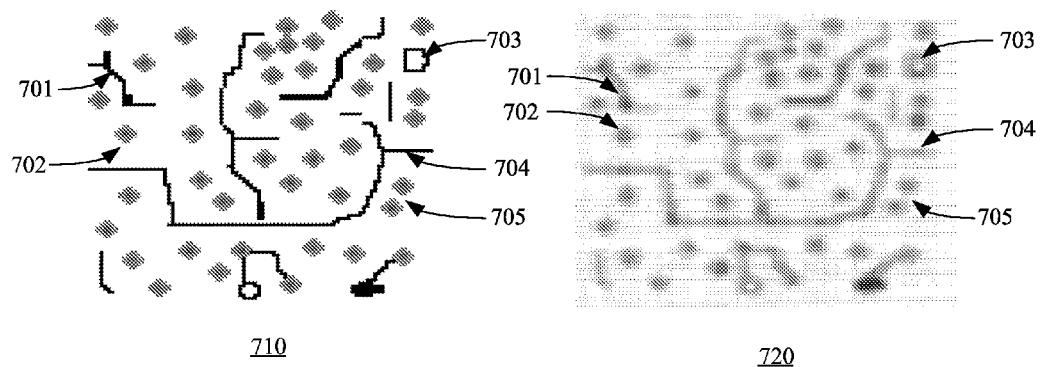
FIG. 7
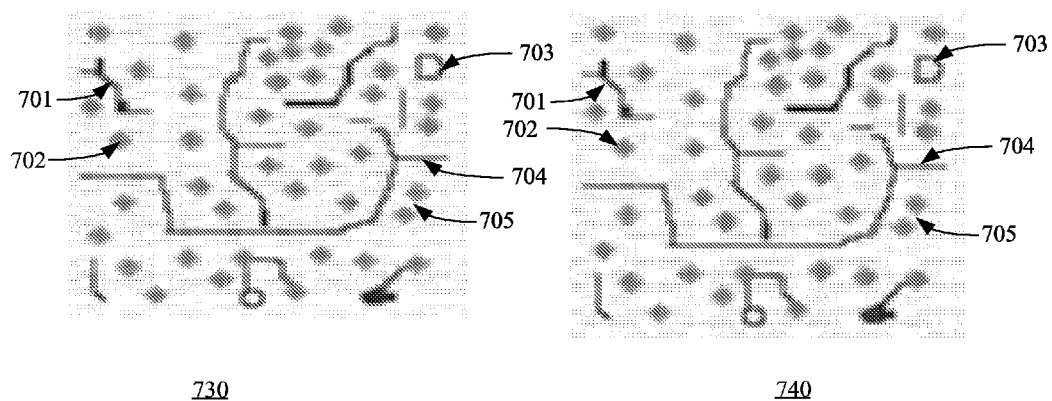

HIGH ASPECT RATIO X-RAY TARGETS AND USES OF SAME

This application claims priority from U.S. Provisional Pat. App. No. 61/981,330, filed Apr. 18, 2014, which is hereby incorporated by reference in its entirety.

TECHNICAL FIELD OF THE INVENTION

The present invention relates to x-ray targets designed to increase both the resolution and throughput of imaging systems incorporating them, such as x-ray tomography systems, and including both thick and thin x-ray targets for alternate low and high resolution scans, Hadamard patterned targets for image multiplexing and improved resolution, and targets made of different hard x-ray producing materials for energy dependent imaging.

BACKGROUND OF THE INVENTION

An x-ray tomography system can provide an image of the internal structure of a sample without having to destroy or cross-section the sample. X-rays produced by the system are passed through the sample and detected by an x-ray detector to obtain an absorption image from a cross-section of the sample. The x-ray detector can be 2 dimensional, in which case multiple cross-sectional images can be obtained at the same time. The sample and or x-ray source and detector are incrementally rotated, and additional cross sectional images are obtained from different angles. Multiple cross-sectional images obtained in this manner are mathematically manipulated to obtain sample information to reconstruct an image of the interior of the sample.

Two important parameters of an x-ray tomography system are its resolution and its throughput. The resolution refers to how small a feature the system can image, and the throughput refers to how fast the system can acquire an image. Throughput can be increased by increasing the flux of x-rays passed through the sample, however, this typically decreases the resolution. X-ray tomography system designs are therefore often a compromise between throughput and resolution. While some high resolution systems have been described in academic literature, they typically require an undesirably long image acquisition time.

In commercial x-ray tomography systems, x-rays are typically generated by directing a high energy beam of electrons toward a target. As the electrons come to rest, they produce x-rays known as bremsstrahlung having frequencies that lie along a continuous frequency spectrum. In addition, some of the electrons collide with and eject electrons in the inner shells of the target atoms. The vacancies created by these ejected electrons are subsequently filled by electrons in the outer shells of the target atoms, which drop in energy level by spontaneously emitting characteristic x-rays whose energies are determined by the differences between the energy levels of the inner and outer shell electrons. Both types of x-rays can contribute to x-ray imaging, however the flux of characteristic x-rays is typically much larger than the flux of bremsstrahlung, and so characteristic or hard x-rays typically contribute more to the x-ray absorption images.

The resolution of an x-ray tomography system without x-ray focusing optics is determined in large part by the effective size of its x-ray source. For systems that use an electron beam to generate x-rays, the effective source size is determined by the volume within which the beam electrons interact with and come to rest in the target. This interaction volume is largely determined by the density and atomic number of the target material, and the diameter and energy of the electron beam, and is typically tear-drop shaped.

An x-ray source for a typical x-ray tomography system 100 is shown in FIG. 1. The source consists of an electron beam 105, and a target 120. The target is typically made by depositing a thin metal film 130 of high atomic number and density (e.g., tungsten) on a substrate 140 of low atomic number and density (e.g., silicon). The target is typically tilted at an angle 150 of about 45 degrees with respect to the electron beam 105. Increasing the energy of electron beam 105 increases the interaction volume within x-ray target 120 (e.g., from a smaller interaction volume 160 to a larger interaction volume 170), thereby increasing the flux of x-rays produced in the target and the throughput of the x-ray tomography system. However, increasing the electron beam energy also increases the effective source size of the x-ray target (e.g., from a smaller effective source size 165 to a larger effective source size 175), thereby decreasing the resolution of the x-ray tomography system.

In some x-ray tomography systems, x-ray optics are used to focus the x-rays produced in the target to reduce the effective source size. However, x-ray optics absorb some of the incoming x-ray flux and typically have a limited depth of focus. As a result, portions of a sample that are not in the focal plane of the x-ray beam but that contribute to the image of the sample tend to decrease the resolution, thereby at least partially offsetting the resolution gains made by focusing the x-ray beam. Moreover, x-ray optics add additional system expense and complexity, including the need to properly align the optical system.

Stand-alone x-ray tomography systems are relatively expensive with prices greater than a million dollars. A much less expensive option is to add a metal target, rotating sample stage, and x-ray detector to a scanning electron microscope (SEM). The electron beam of the SEM can be focused onto the metal target to generate x-rays, which subsequently pass through a sample mounted on the sample stage to an x-ray detector to obtain an absorption image. The absorption images are typically obtained in a projection mode, with the sample positioned between the x-ray source (target) and the x-ray detector. The x-ray flux produced by the electron beam is dependent on the beam energy and the beam current. Because the focusing columns of most SEMs are primarily designed for forming secondary electron images, the electron beam current is typically limited to less than 75 nA and the beam energy is typically limited to 30 keV. The resultant x-ray flux produced by the electron beam of a typical SEM is therefore relatively low, and these systems require relatively long image acquisition times and have limited resolution.

Sasov et al., in "New type of x-ray source for lens-less laboratory nano-CT with 50 nm resolution," Developments in X-ray Tomography VII, Proc. of SPIE Vol. 7804, describes one way to reduce the interaction volume and therefore the effective source size of an x-ray target. Sasov uses a hair-like tip of a metal wire as a target. The tip has its axis pointed in the direction of the detector, which increases the depth from which x-rays are generated, but does not greatly increase the width, thereby increasing the x-ray flux without increasing the effective source size. The x-ray flux generated from a small diameter rod-shaped target, however, is still relatively low, and so image acquisition time would still be long. Sasov et al. does not state an image acquisition time. Sasov's x-ray source also suffers from lack of a heat sink. As the energy and/or flux of electrons used to generate x-rays increases, Sasov's source lacks a mechanism for dissipating the extra heat thereby generated.

Cazaux et al., in "Recent developments in X-ray projection microscopy and X-ray microtomography applied to materials science," Journal de Physique IV, Colloque C7, supplement au Journal de Physique 111, Vol. 3, November 1993, pp. 2099-2104, describes a system in which a target is impacted by an electron beam, and the x-rays produced are transmitted through the target and out of a vacuum chamber toward a sample and a detector. Cazaux' system also allows the target generating the incoming x-ray beam to be changed in a few seconds, allowing different images of the same specimen to be obtained with different characteristic x-rays.

SUMMARY OF THE INVENTION

Disclosed herein is an x-ray target that includes a substrate made from a soft x-ray producing material, and a high aspect ratio structure made from a hard x-ray producing material embedded in or formed on the substrate. The high aspect ratio structure includes a plurality of high aspect ratio structures arranged in one or more grids or arrays, and the high aspect ratio structures in one of the one or more grids or arrays are arranged to form a Hadamard matrix structure.

Further disclosed herein is a method for generating an x-ray image of a sample, the method including: sequentially focusing an electron beam on each of a plurality of orthogonal Hadamard matrix structures, each orthogonal Hadamard matrix structure made from a plurality of high aspect ratio structures arranged at different pixel locations in a pixilated grid pattern, each high aspect ratio structure made from a hard x-ray producing material; illuminating the sample with x-rays produced by sequentially focusing the electron beam on each of the plurality of orthogonal Hadamard matrix structures; sequentially detecting the x-rays transmitted through the sample, and recording the detected x-rays in a plurality of Hadamard transformed x-ray images; applying one or more inverse Hadamard transforms to the plurality of Hadamard transformed x-ray images to generate one or more x-ray images, wherein each of the one or more x-ray images is generated from an inverse Hadamard transform corresponding to a different pixel in the pixilated grid of high aspect ratio structures that make up the orthogonal Hadamard matrix structures; and combining the one or more x-ray images to generate an x-ray image of the sample.

Further disclosed herein is a computer program product, embedded on a non-transitory medium. The computer program product includes instructions operable to cause a programmable processor to sequentially focus an electron beam on each of a plurality of orthogonal Hadamard matrix structures, each orthogonal Hadamard matrix structure made from a plurality of high aspect ratio structures arranged at different pixel locations in a pixilated grid pattern, each high aspect ratio structure made from a hard x-ray producing material; sequentially detect x-rays produced by the plurality of orthogonal Hadamard matrix structures and transmitted through the sample, and record the detected x-rays in a plurality of Hadamard transformed x-ray images; apply one or more inverse Hadamard transforms to the plurality of Hadamard transformed x-ray images to generate one or more x-ray images, wherein each of the one or more x-ray images is generated from an inverse Hadamard transform corresponding to a different pixel in the pixilated grid of high aspect ratio structures that make up the orthogonal Hadamard matrix structures; and combine the one or more x-ray images to generate an x-ray image of the sample.

Also disclosed herein is a method for generating an x-ray image of a sample, the method including: raster scanning the sample with a focused electron beam to image the sample; raster scanning an x-ray target with the focused electron beam to image the x-ray target and to locate a plurality of hard x-ray producing structures located on or embedded within the x-ray target; illuminating one or more of the plurality of hard x-ray producing structures with an electron beam to generate a flux of x-rays; detecting x-rays that pass through the sample at an x-ray detector; and recording an x-ray image of the sample from the detected x-rays.

Additionally disclosed herein is an x-ray projection system that includes a planar x-ray target, a sample holder; and a planar x-ray detector. The plane of the planar x-ray detector is substantially parallel to the plane of the planar x-ray target. The planar x-ray target, the sample holder and the planar x-ray detector are substantially aligned along an axis that is substantially perpendicular to the plane of the x-ray target.

The foregoing has outlined rather broadly the features and technical advantages of the present invention in order that the detailed description of the invention that follows may be better understood. Additional features and advantages of the invention will be described hereinafter. It should be appreciated by those skilled in the art that the conception and specific embodiments disclosed may be readily utilized as a basis for modifying or designing other structures for carrying out the same purposes of the present invention. It should also be realized by those skilled in the art that such equivalent constructions do not depart from the scope of the invention as set forth in the appended claims.

BRIEF DESCRIPTION OF THE DRAWINGS

For a more thorough understanding of the present invention, and advantages thereof, reference is now made to the following descriptions taken in conjunction with the accompanying drawings, in which:

FIG. 7 is an illustration of a simulated sample, and images of that sample taken with various virtual x-ray targets.

DETAILED DESCRIPTION OF PREFERRED EMBODIMENTS

Various embodiments of the present invention provide x-ray targets designed to increase both the resolution and throughput of imaging systems incorporating them, such as x-ray tomography systems, and including both thick and thin x-ray targets for alternate low and high resolution scans, Hadamard patterned targets for image multiplexing and improved resolution, and targets made of different hard x-ray producing materials for energy dependent imaging.

Figure 2:
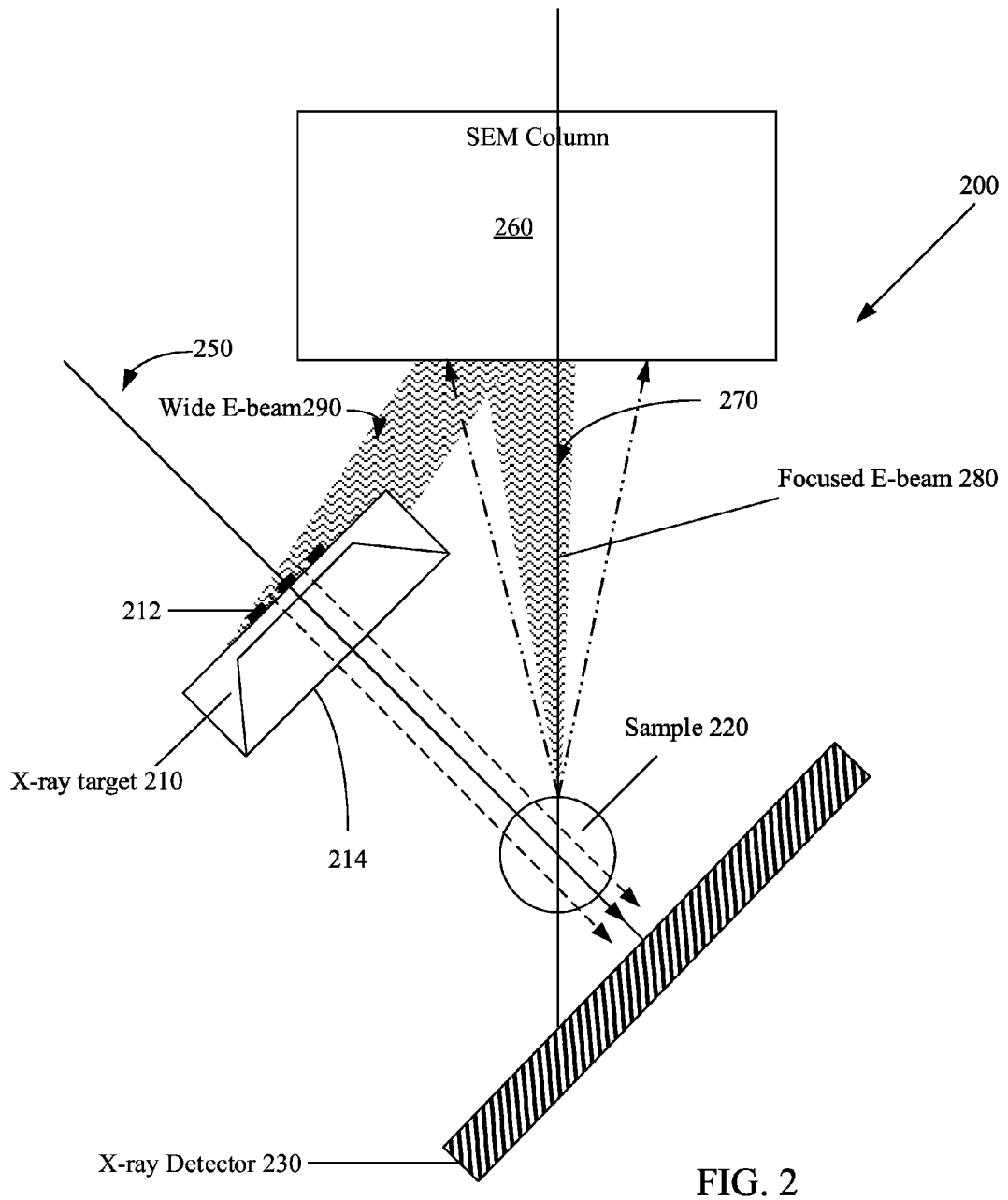
FIG. 2 is an illustration of an x-ray tomography system according to an embodiment of the disclosure.

FIG. 2 discloses one embodiment of an x-ray tomography system 200 with a planar target 210, sample 220, and planar detector 230, wherein the planes of the target 210 and detector 230 are generally parallel, and the centers of the target 210, sample 220, and detector 230 fall generally on an axis 250 that is perpendicular to the planes of the target 210 and detector 230. The x-ray tomography system 200 includes an SEM or scanning electron microscope having an optical column 260 whose axis 270 is oriented with respect to the axis 250 of the target 210, sample 220, and detector 230 to enable alternative imaging of the sample 220 and target 210 with a focused electron beam 280, and illumination of the target 210 or portions of the target 210 with a wider electron beam 290.

The x-ray producing target 210 may be designed to have a number of independent x-ray producing structures 212 arranged in a pattern, which may be an N×M grid or matrix, where N and M are integers. The target 210 may also contain multiple grids of x-ray producing structures 212 as further explained below. The target 210 may be fabricated using various techniques that are used in semiconductor manufacturing including deposition, lithography and etch, and in its simplest form (i.e., a single x-ray producing structure 212) can also be fabricated using standard transmission electron microscope (TEM) lamella preparation techniques. The SEM column 260 may use a focused electron beam 280 to image the target 210 to determine its orientation and the locations of the x-ray producing structures 212 or grids of x-ray producing structures 212 that it contains. Each of the x-ray producing structures 212 may subsequently be separately illuminated with the focused electron beam 280 such that only a single structure 212 is illuminated. Alternatively, each of the grids of x-ray producing structures 212 may be separately illuminated with the wide electron beam 290 such that all of the x-ray producing structures 212 in any given grid are illuminated.

While the x-ray producing structures 212 or a grid of x-ray producing structures 212 in the target 210 may be illuminated from any angle, including from a second SEM column (not shown) directly behind the target 210, the x-rays produced in the structures 212 that illuminate the sample 220 will exit target 210 in a direction that is generally parallel to the target-sample-detector axis 250. The target 210 is thus elongated in the direction of axis 250 in order to increase the x-ray flux while maintaining a small cross section in the direction of axis 250.

In particular, the x-ray producing structures 212 are made as high aspect ratio (>2) pillars or posts that sit on top of or are embedded within a target substrate, and may be constructed with diameters less than 50 nm and lengths of more than 100 nm. The small diameters of the high aspect ratio structures 212 determine the effective source size of the target 210 since only x-rays that are emitted in a generally longitudinal direction (i.e., along the target-sample-detector axis 250) are used to illuminate the sample 220. The lengths of the high aspect ratio structures 212 determine, in part, the x-ray flux since the entire length of the structures 212 contribute to x-ray production when the structures 212 are illuminated with electron beams.

In one embodiment, shown in FIG. 2, the x-ray producing structures 212 are situated on or in target 210 such that they face away from the sample 220 and detector 230. In this embodiment, the x-ray flux from the target 210 can be increased by etching away a portion 214 of the target substrate that lies between the x-ray producing structures 212 and the sample 220. In an alternative embodiment (not shown), the x-ray producing structures 212 can be situated on or in target 210 such that they directly face the sample 220 and detector 230. In this embodiment, no advantages are achieved by etching away portion 214, and the extra substrate material can help dissipate heat produced by the x-ray producing structures 212 when they are illuminated with the electron beam.

Figure 3A:
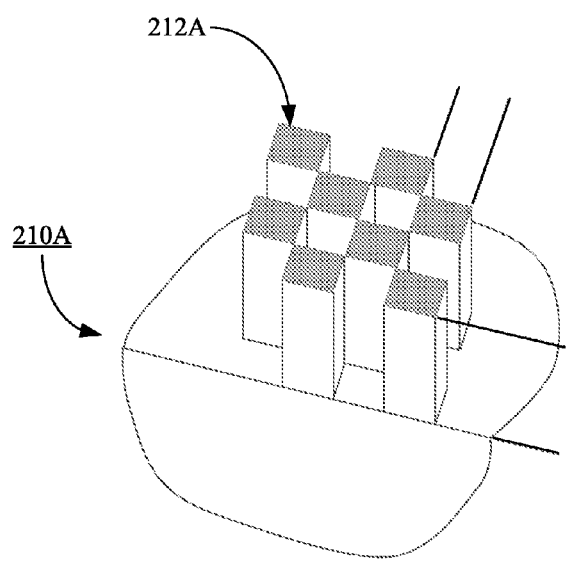
FIGS. 3A and 3B are illustrations of high aspect ratio x-ray producing structures in an electron beam target according to embodiments of the disclosure.
Figure 3B:
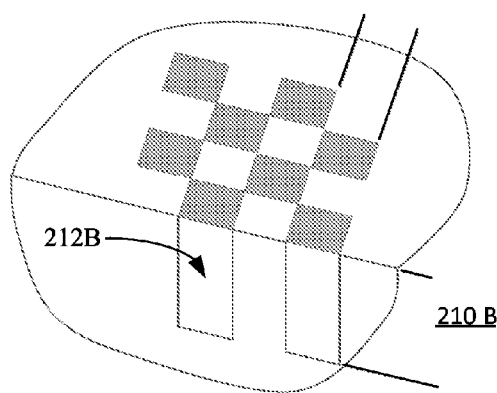

As shown in FIGS. 3A and 3B, different methods may be used to create the x-ray producing structures 212 in the target 210. According to a first method, used to produce the target structures 212A shown in FIG. 3A, a thin film of a high atomic number metal (e.g., W) is deposited on a substrate of a low atomic number material such as Si. A layer of photoresist is spun onto the metal surface, patterned using conventional optical or electron beam lithography, and developed. An anisotropic etch, such as a deep reactive ion etch, transfers the pattern to the underlying metal layer by etching the metal layer, thereby creating a pattern of high aspect ratio metal posts or columns on top of the substrate. The developed photoresist remaining on top of the metal posts or pillars is stripped away, leaving the target 210 as a pattern of raised x-ray producing structures 212A. Optionally, an oxide film can be deposited to fill in the spaces between the metal pillars or posts (e.g., using a CVD or other suitable process), and the surface of the target can be made smooth via chemical mechanical polishing.

According to a second method, used to produce the target structures 212B shown in FIG. 3B, a layer of photoresist is spun onto a low atomic number substrate (e.g., Si), patterned as before, and developed. An anisotropic etch transfers the pattern to the substrate by etching the substrate to create a pattern of high aspect ratio wells or bores in the substrate. These bores are subsequently filled with a high atomic number hard x-ray producing material (e.g., W) using conventional deposition techniques such as CVD, PVD or electrochemical plating. Optionally, the walls of the bores can be coated with a barrier layer or metal prior to the deposition of the x-ray producing material to prevent the x-ray producing material's diffusion into the substrate. Finally, the developed photoresist can be stripped away, and the entire structure made smooth via chemical mechanical polishing. The final structure of the target 210 will then consist of a low atomic number substrate (e.g., Si), embedded with a pattern of x-ray producing structures 212B, consisting of high aspect ratio posts or columns of a high atomic number material (e.g., W).

A number of different patterns can be formed in the target 210. One such pattern can be in the form of a grid or N×M matrix, where different pixels or cells in the grid can have different x-ray production properties. For example, different pixels can contain different x-ray producing materials (e.g., W, Au, Pb or V), thereby producing x-rays with different characteristic frequencies. Different pixels can also contain different sizes of x-ray producing structures 212. For example, some structures 212 can have a larger diameter or cross-sectional area than others. For fixed length x-ray producing structures 212, those having larger cross-sectional areas will produce larger x-ray fluxes and therefore increase the throughput of the x-ray tomography system 200. Such larger cross-sectional area structures 212 or grids of such structures can be used to quickly produce low resolution images of sample 220. Finer resolution images of sample 220 or portions of sample 220 can subsequently be produced by focusing the wide electron beam 190 on smaller cross-sectional area structures 212 or grids of such structures.

Another pattern that can be formed in target 210 is a grid or array of identical x-ray producing structures 212. Such a pattern can be useful for dispersing the heat generated in the x-ray producing structures 212 when they are illuminated with an electron beam. For example, if a given procedure requires illuminating an x-ray producing structure 212 for t seconds, thereby depositing Q Joules of energy into the x-ray producing structure 212, the same procedure can be conducted by illuminating each of a plurality of N identical x-ray producing structures 212 for t/N seconds, thereby depositing only Q/N Joules of energy into each x-ray producing structure 212. By sequentially illuminating a plurality of identical x-ray producing structures 212 in this way, the overall system flux can be increased since each x-ray producing structure 212 can carry and dissipate its maximum heat load while the electron beam cycles through the plurality of identical x-ray producing structures.

In some embodiments, the x-ray producing structures 212 in the target 210 can be arranged to produce a Hadamard matrix structure or a plurality of orthogonal Hadamard matrix structures. In such targets, which can be arranged as 2×2, 4×4, 8×8, or similarly dimensioned matrices, approximately half the target pixels are formed as posts or pillars of hard x-ray producing materials (e.g., W). The remaining pixels can either be formed as posts or pillars of a soft x-ray producing substrate (e.g., Si) when the hard x-ray producing materials are embedded in the substrate, or from the vacuum itself when the hard x-ray producing materials sit on top of the substrate. As used herein, a hard x-ray producing material means a material producing characteristic x-rays having an energies greater than 5-10 keV, while a soft x-ray producing material means a material producing characteristic x-rays having energies less than 5-10 keV.

Figure 8:
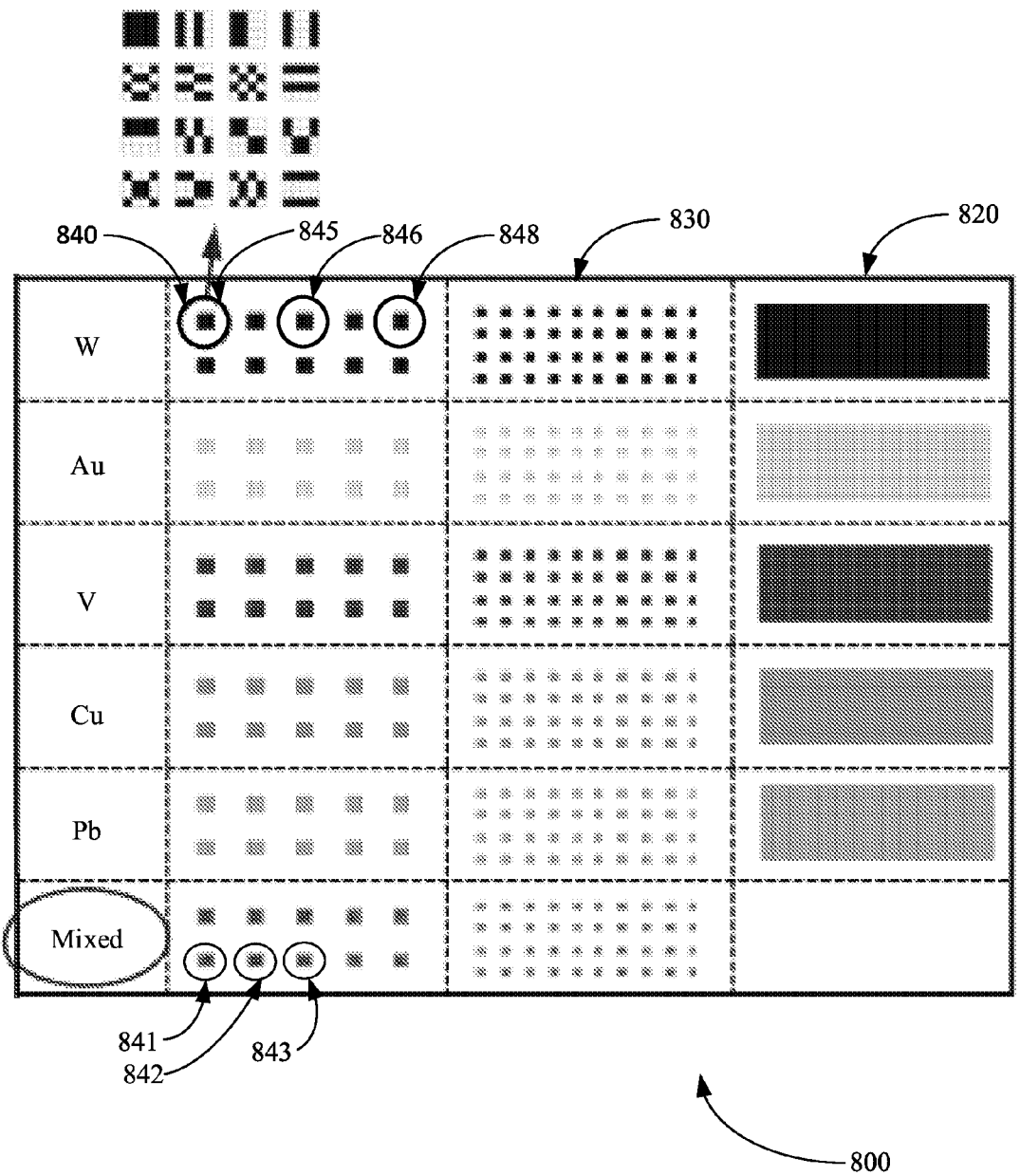
FIG. 8 is an illustration of an exemplary electron beam target for use in an x-ray tomography system according to an embodiment of the disclosure.

There are several potential advantages of the lithographically-patterned x-ray targets illustrated in FIGS. 3A and 3B over the needle target as described in Sasov. One advantage is that because the target is lithographically patterned into a large target area, a large multiplicity of targets of varying sizes and target materials may be configured within the overall target structure as shown in FIG. 8. This differs from the single needle-like target (of a single material) shown in FIG. 7 of Sasov's paper. In addition, the needle-like target of Sasov has minimal heat-sinking since it is a free-standing structure extending out into the vacuum of the SEM. Also, the exact dimensions of Sasov's needle are likely to be unpredictable and possibly changing over the lifetime of the x-ray source due to ablation or contamination effects on the needle.

Figure 4:
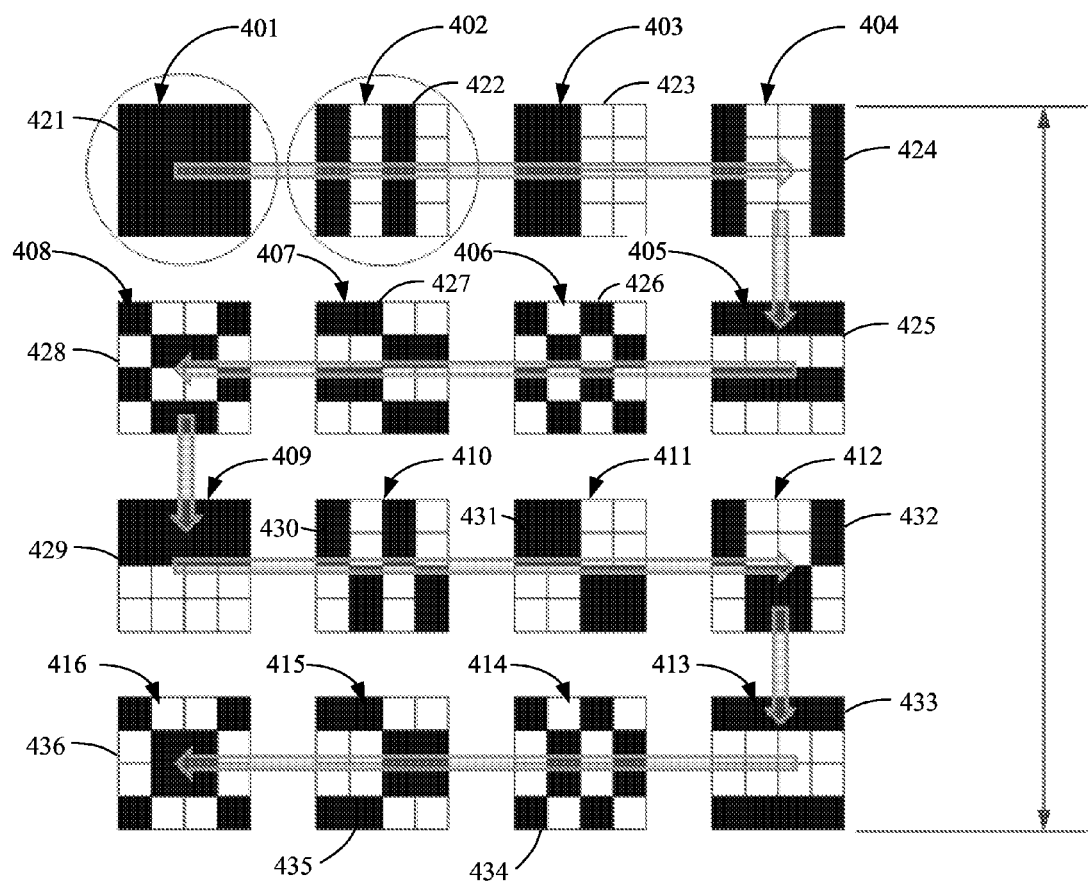
FIG. 4 is an illustration of a plurality of Hadamard matrices constructed on an electron beam target from a plurality of grids of high aspect ratio x-ray producing structures according to an embodiment of the disclosure.

As shown in FIG. 4, sixteen orthogonal Hadamard matrices 401-416 can be constructed as separately targetable grids 421-436 on a target 210, where each Hadamard matrix consists of a 4×4 array of either hard (black) or soft (white) x-ray producing structures 212. In some embodiments, a total of $N^2$ separately targetable Hadamard matrix structures can be constructed on the target 210, where each Hadamard matrix structure has a dimension of N×N (i.e., consists of an N×N grid of x-ray producing structures 212). The Hadamard matrices can be constructed on the target 210 so that corresponding pixels from each of the $N^2$ Hadamard matrices produce a Hadamard code of length $N^2$. Thus, the set of $N^2$ orthogonal Hadamard matrices constructed on the target 210 can produce a total of $N^2$ orthogonal Hadamard codes (one per pixel), where each code is of length $N^2$. As used herein, the term Hadamard matrix and Hadamard code are used to refer to a set of $N^2$ matrices corresponding to a set of $N^2$ orthogonal codes, each code of length $N^2$, where the pixel values for the mth matrix are obtained from the mth values of the $N^2$ orthogonal codes, regardless of whether the matrices and codes conform to a mathematically strict definition of Hadamard matrices and codes.

In Tables 1 and 2 below, a list of Hadamard codes is disclosed that can be used to construct a grid of four 2×2 Hadamard matrix structures or a grid of sixteen 4×4 Hadamard matrix structures on target 210.

TABLE 1

| Code | M1 | M2 | M3 | M4 | Row | Col. |
|---|---|---|---|---|---|---|
| H1 | 1 | 1 | 1 | 1 | 1 | 1 |
| H2 | 1 | −1 | −1 | 1 | 1 | 2 |
| H3 | 1 | 1 | −1 | −1 | 2 | 1 |
| H4 | 1 | −1 | 1 | −1 | 2 | 2 |

TABLE 2

| | M | | | | | | | | | | | | | | | | | |
|---|---|---|---|---|---|---|---|---|---|---|---|---|---|---|---|---|---|---|
| C | 1 | 2 | 3 | 4 | 5 | 6 | 7 | 8 | 9 | 10 | 11 | 12 | 13 | 14 | 15 | 16 | R | C |
| H1 | 1 | 1 | 1 | 1 | 1 | 1 | 1 | 1 | 1 | 1 | 1 | 1 | 1 | 1 | 1 | 1 | 1 | 1 |
| H2 | 1 | −1 | 1 | −1 | 1 | −1 | 1 | −1 | 1 | −1 | 1 | −1 | 1 | −1 | 1 | −1 | 1 | 2 |
| H3 | 1 | 1 | −1 | −1 | 1 | 1 | −1 | −1 | 1 | 1 | −1 | −1 | 1 | 1 | −1 | −1 | 1 | 3 |
| H4 | 1 | −1 | −1 | 1 | 1 | −1 | −1 | 1 | 1 | −1 | −1 | 1 | 1 | −1 | −1 | 1 | 1 | 4 |
| H5 | 1 | 1 | 1 | 1 | −1 | −1 | −1 | −1 | 1 | 1 | 1 | 1 | −1 | −1 | −1 | −1 | 2 | 1 |
| H6 | 1 | −1 | 1 | −1 | −1 | 1 | −1 | 1 | 1 | −1 | 1 | −1 | −1 | 1 | −1 | 1 | 2 | 2 |
| H7 | 1 | 1 | −1 | −1 | −1 | −1 | 1 | 1 | 1 | 1 | −1 | −1 | −1 | −1 | 1 | 1 | 2 | 3 |
| H8 | 1 | −1 | −1 | 1 | −1 | 1 | 1 | −1 | 1 | −1 | −1 | 1 | −1 | 1 | 1 | −1 | 2 | 4 |

TABLE 2-continued

| C | 1 | 2 | 3 | 4 | 5 | 6 | 7 | 8 | 9 | 10 | 11 | 12 | 13 | 14 | 15 | 16 | R | C |
|---|---|---|---|---|---|---|---|---|---|----|----|----|----|----|----|----|---|---|
| H9 | 1 | 1 | 1 | 1 | 1 | 1 | 1 | 1 | −1 | −1 | −1 | −1 | −1 | −1 | −1 | −1 | 3 | 1 |
| H10 | 1 | −1 | 1 | −1 | 1 | −1 | 1 | −1 | −1 | 1 | −1 | 1 | −1 | 1 | −1 | 1 | 3 | 2 |
| H11 | 1 | 1 | −1 | −1 | 1 | 1 | −1 | −1 | −1 | −1 | 1 | 1 | −1 | −1 | 1 | 1 | 3 | 3 |
| H12 | 1 | −1 | −1 | 1 | 1 | −1 | −1 | 1 | −1 | 1 | 1 | −1 | −1 | 1 | 1 | −1 | 3 | 4 |
| H13 | 1 | 1 | 1 | 1 | −1 | −1 | −1 | −1 | −1 | −1 | −1 | −1 | 1 | 1 | 1 | 1 | 4 | 1 |
| H14 | 1 | −1 | 1 | −1 | −1 | 1 | −1 | 1 | −1 | 1 | −1 | 1 | 1 | −1 | 1 | −1 | 4 | 2 |
| H15 | 1 | 1 | −1 | −1 | −1 | −1 | 1 | 1 | −1 | −1 | 1 | 1 | 1 | 1 | −1 | −1 | 4 | 3 |
| H16 | 1 | −1 | −1 | 1 | −1 | 1 | 1 | −1 | −1 | 1 | 1 | −1 | 1 | −1 | −1 | 1 | 4 | 4 |

Figure 5:
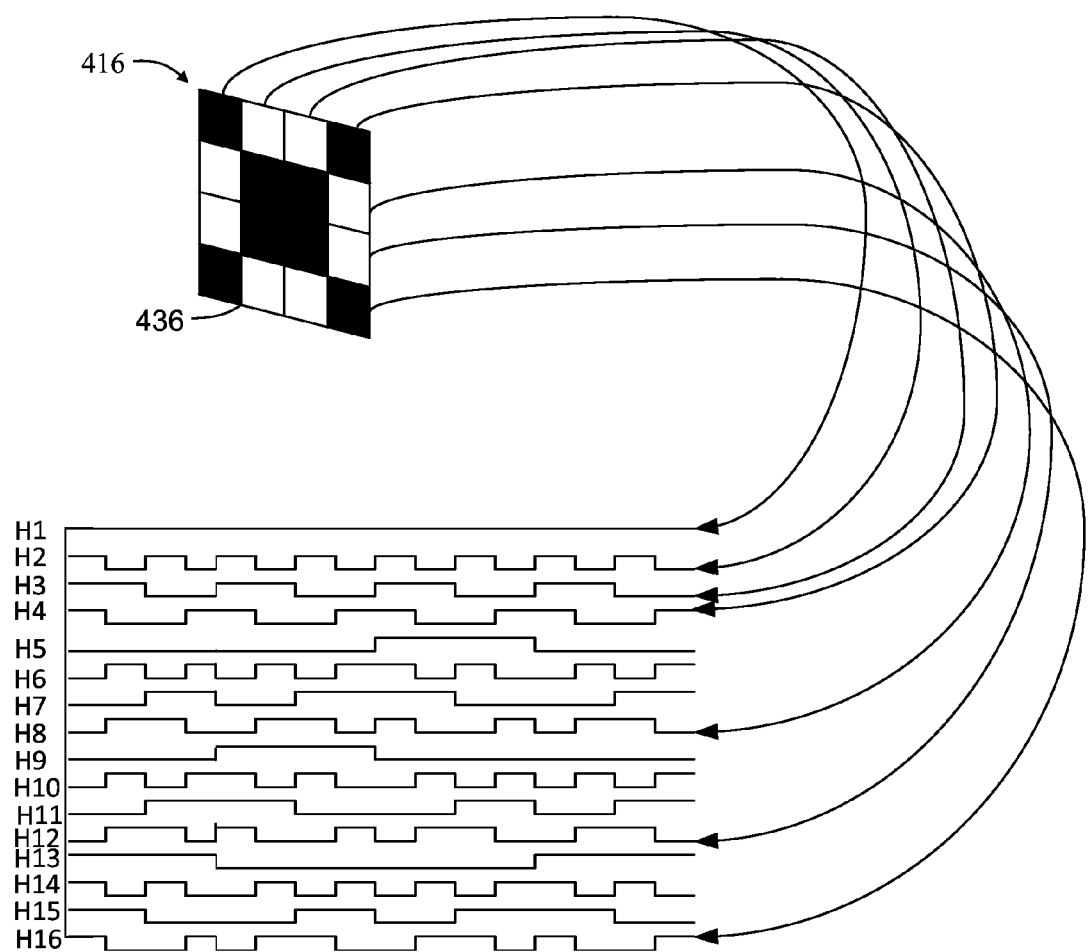
FIG. 5 is an illustration of a particular Hadamard matrix constructed on an electron beam target from a grid of high aspect ratio x-ray producing structures according to an embodiment of the disclosure.

FIG. 5 is an illustration of a particular Hadamard matrix constructed on an electron beam target from a grid of high aspect ratio x-ray producing structures. The particular Hadamard matrix shown is Hadamard matrix 416 of grid 436 shown in FIG. 4. It can be constructed from the entries in the $16^{th}$ column of Table 2. As shown, the first row (R1) of Hadamard matrix structure 416 contains respective entries of 1, −1, −1 and 1 in columns C1-C4. Here, an entry of 1 for a pixel in Hadamard matrix structure 416 indicates that the x-ray producing structure 212 constructed at a location on target 210 corresponding to that pixel is made from a hard x-ray producing material (e.g., W). Similarly, an entry of −1 for a pixel in Hadamard matrix structure 416 indicates that the x-ray producing structure 212 constructed at a location on target 210 corresponding to that pixel is made from a soft x-ray producing substrate (e.g., Si) when the hard x-ray producing material is embedded in the substrate, or the vacuum when the hard x-ray producing material sits on top of the substrate. Referring again to Table 2, the second row (R2) of Hadamard matrix structure 416 contains respective entries of −1, 1, 1 and −1 in columns C1-C4, the third row (R3) of Hadamard matrix structure 416 contains respective entries of −1, 1, 1 and −1 in columns C1-C4, and the fourth row (R4) of Hadamard matrix structure 416 contains respective entries of 1, −1, −1 and 1 in columns C1-C4.

As noted above, the x-ray tomography system 200 can use a focused electron beam 280 to image the target 210 to determine its orientation and the locations of the x-ray producing structures 212 it contains, including the grids 421-436 of x-ray producing structures 212 constructed in the form of Hadamard matrices 401-416. Subsequently, as shown in FIG. 4, the x-ray tomography system 200 can use a wide electron beam 290 to separately illuminate all of the x-ray producing structures 212 in any one of the Hadamard matrix structures 401-416. The x-ray tomography system 200 can therefore sequentially step through each of the sixteen Hadamard matrix structures 401-416 that are constructed on target 210 to collect sixteen Hadamard transformed images of sample 220.

Once all sixteen Hadamard transformed images are obtained, the Hadamard codes H1 through H16 shown in Table 2 can be used to apply inverse Hadamard transforms to the images, thereby obtaining sixteen normal images of the sample. Since each of the Hadamard codes H1 to H16 correspond to different pixels in the Hadamard matrices 401-416, each of the sixteen normal images of the sample will correspond to images taken from different pixel locations. Once obtained, the sixteen normal images can be combined to obtain an overall image of the sample. In this way, the wide electron beam 290 is able to illuminate a target structure of a given size (e.g., a 200 nm Hadamard matrix structure), while obtaining a sample image having a resolution corresponding to a target structure having an effective size that is a fraction of its given size (e.g., 50 nm for a 4×4 Hadamard matrix structure). This allows higher resolution sample images to be obtained without reducing the throughput of the x-ray tomography system 200.

Figure 6:
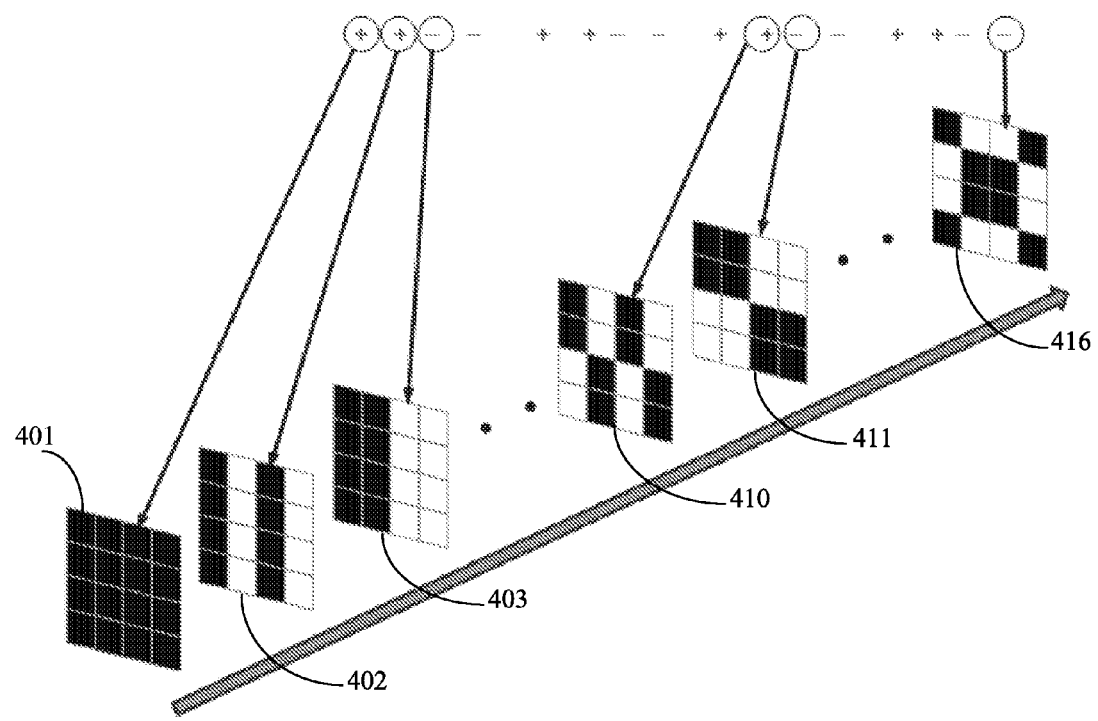
FIG. 6 is an illustration of a method for obtaining a normal image of a sample by applying an inverse Hadamard transform to the Hadamard transformed images of the sample according to an embodiment of the disclosure.

FIG. 6 is an illustration of a method for obtaining a normal image of a sample by applying an inverse Hadamard transform to the Hadamard transformed images of the sample. In particular, FIG. 6 illustrates how a normal image of sample 210, as seen from the location of the pixel in the $1^{st}$ row and $3^{rd}$ column of Hadamard matrix 401, can be obtained by applying an inverse Hadamard transform to the images that were sequentially obtained by illuminating the sample with x-rays produced by the Hadamard matrix structures 401-416.

The inverse Hadamard transform for a given pixel essentially amounts to adding or subtracting the Hadamard transformed images of the sample using the Hadamard code for that pixel. As shown in Table 2, the Hadamard code for the pixel in the $1^{st}$ row and $3^{rd}$ column is H3. Thus, the normal image of the sample as seen from that pixel can be obtained by applying Hadamard code H3 to the images obtained for the sample from each of the Hadamard matrix structures 401-416. This amounts to adding the images obtained from the Hadamard matrix structures 410-416 according to the H3 sequence, namely, +1(401)+1(402)−1(403)−1(404)+1(405)+1(406)−1(407)−1(408)+1(409)+1(410)−1(411)−1(412)+1(413)+1(414)−1(415)−1(416). That is to say, the normal image for the pixel in the $1^{st}$ row and $3^{rd}$ column is obtained by adding the images obtained from the Hadamard matrix structures 401, 402, 405, 406, 409, 410, 413 and 414, and subtracting the images obtained from the Hadamard matrix structures 403, 404, 407, 408, 411, 412, 415 and 416. Prior to adding the images according to the relevant Hadamard code, the images can be adjusted to correct for the relative parallax introduced since each of the Hadamard matrix structures 401-416 are constructed at different locations in the target 210. The same procedure can then be applied to obtain the normal images of the sample as seen from the other 15 pixels. Namely, for each pixel, the appropriate Hadamard code for that pixel is used to add the images of the sample obtained by illuminating the Hadamard matrix structures 401-416.

FIG. 7 is an illustration of a simulated sample, and images of that sample taken with various virtual x-ray targets. The simulated sample 710 contains 10,000 pixels arranged in a 100×100 grid, where each pixel was assigned a uniform 5% x-ray absorption to represent a solid object. Various features, such as features 701-705 ranging in size from 50 nm to several hundred nm, were added to the simulated sample 710 and given x-ray absorptions ranging between 5% and 100%. Features having larger x-ray absorption appear darker in the simulated sample 710. The simulated sample 710 was subsequently imaged using a 200 nm un-patterned target (image 720), a 50 nm un-patterned target (image 730), and a target patterned with sixteen 200 nm 4×4 Hadamard matrices, each having a 50 nm pixel size (image 740 after applying inverse Hadamard transforms and combining the images obtained). All of the features 701-705 in the simulated sample 710 are visible in images 720 through 730. The resolution of image 720 (200 nm un-patterned target) is obviously reduced relative to the resolution of image 730 (50 nm un-patterned target). By contrast, the resolution of image 740 (target patterned with 200 nm Hadamard matrices) has about the same resolution as image 730 (50 nm un-patterned target). The x-ray flux from the target patterned with the 200 nm Hadamard matrices was approximately 8× that of the 50 nm un-patterned target since approximately half of the sixteen pixels in the Hadamard matrix target structures are illuminated. Thus, the acquisition time for image 730 (50 nm un-patterned target) is approximately 8× the acquisition time for image 740 (target patterned with 200 nm Hadamard matrices).

FIG. 8 is an illustration of an exemplary electron beam target for use in an x-ray tomography system. The target 800, which can be used as the target 210 shown in FIG. 2, contains a plurality of structures having a number of attributes. Each of the structures can be separately imaged and located by the x-ray tomography system 200 using the focused electron beam 280, and each structure can be separately illuminated with the focused electron beam 280 or wide electron beam 290 to produce x-rays to image sample 220.

One attribute of the structures shown in target 800 is the hard x-ray producing material from which they are made. Suitable materials can include Tungsten (W), Gold (Au), Vanadium (V), Copper (Cu) and Lead (Pb), among others. Structures made from different materials can be used to image different components or structures in sample 220 that are sensitive to the different characteristic x-rays produced by the different materials.

Figure 1:
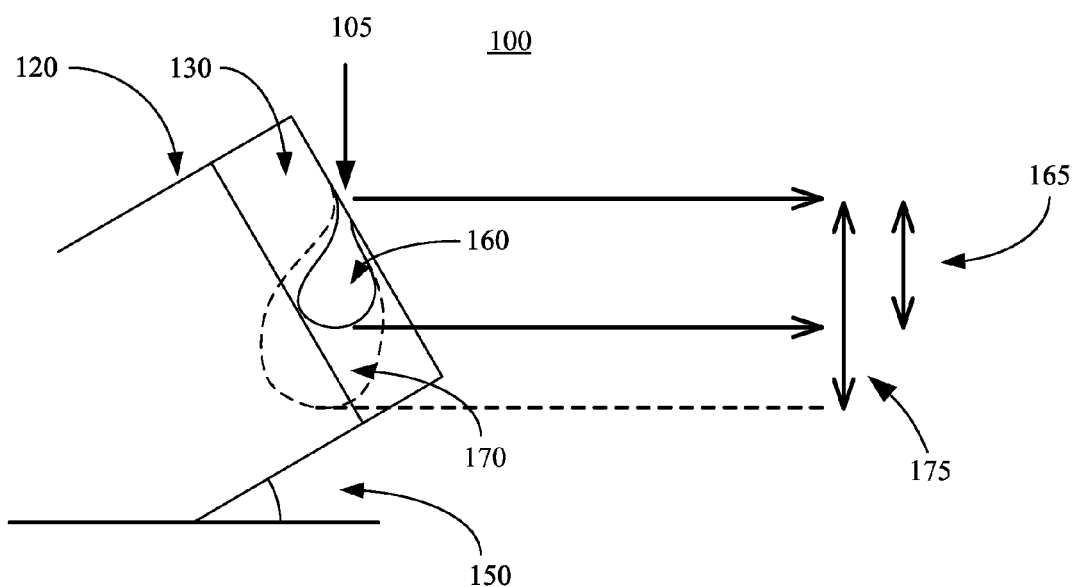
FIG. 1 shows an x-ray source for a typical x-ray tomography system.

A second attribute of the structures shown in target 800 is whether or not they are patterned to contain the high aspect ratio hard x-ray producing structures 212 shown in FIG. 2. Some structures 820 are not. They are simply made from thin layers of metal deposited on a soft x-ray producing substrate (e.g., Si). The effective source size of un-patterned structures 820 will be related to the x-ray fluxes they produce as shown in FIG. 1. By contrast, other structures in target 800, like structures 830 and 840, are patterned to contain high aspect ratio hard x-ray producing structures 212. The effective source size of the patterned structures 830 and 840 will depend only on their cross-sectional area, and will be independent of the x-ray fluxes they produce.

A third attribute of the structures shown in target 800 is the characteristic size or effective cross-sectional areas of the patterned x-ray producing structures 212 they contain. For example, structures 830 can contain small cross-sectional area x-ray producing structures 212, e.g., those having a characteristic size of less than 50 nm. Such structures 830 can be used to form high resolution images of sample 220. By contrast, structures 840 can contain large cross-sectional area x-ray producing structures 212, e.g., those having a characteristic width of more than 100 nm. For example, structure 841 may contain one or more x-ray producing structures 212 having a characteristic width of 300 nm, structure 842 may contain one or more x-ray producing structures 212 having a characteristic width of 200 nm, and structure 843 may contain one or more x-ray producing structures 212 having a characteristic width of 100 nm. Such structures 840 can be used to rapidly acquire lower resolution images of sample 220.

A fourth attribute of the structures shown in target 800 is the nature of the pattern, if any, formed by the x-ray producing structures 212 they contain. For example, the patterned low resolution structures 845, 846 and 848 can contain x-ray producing structures 212 patterned to form grids of Hadamard matrices. Thus, the x-ray producing structures 212 in structure 845 may be patterned to form a grid of sixteen 4×4 Hadamard matrices such as the Hadamard matrices 401-416 shown in FIG. 4; the x-ray producing structures 212 in structure 846 may be patterned to form a grid of sixty four 8×8 Hadamard matrices (not shown); and the x-ray producing structures 212 in structure 848 may be patterned to form a grid of four 2×2 Hadamard matrices (not shown).

Many of the target structures on target 800 can be made from a single hard x-ray producing material (e.g., W). However, some of the structures can be made from two or more materials. This can be particularly useful when the structures are patterned to form Hadamard matrices. For example, if the x-ray producing structures 212 are patterned to form the pixels of a Hadamard matrix, then different pixels (i.e., x-ray producing structures 212) can be made from different materials. If corresponding pixels in a set of Hadamard matrices are made using the same materials (e.g., $1^{st}$ row Au, $2^{nd}$ row Pb, $3^{rd}$ row W, $4^{th}$ row V), separate images of the sample can be obtained showing the sensitivity of the sample or structures within the sample to the different characteristic x-rays produced by the different materials. This is because the inverse Hadamard transform of the images of the sample taken with the Hadamard matrices essentially de-multiplexes the images on a per pixel basis as explained above. Thus, the inverse Hadamard transformed images corresponding to the pixels made from Au, Pb, W and V can be separately obtained and combined.

Figure 9:
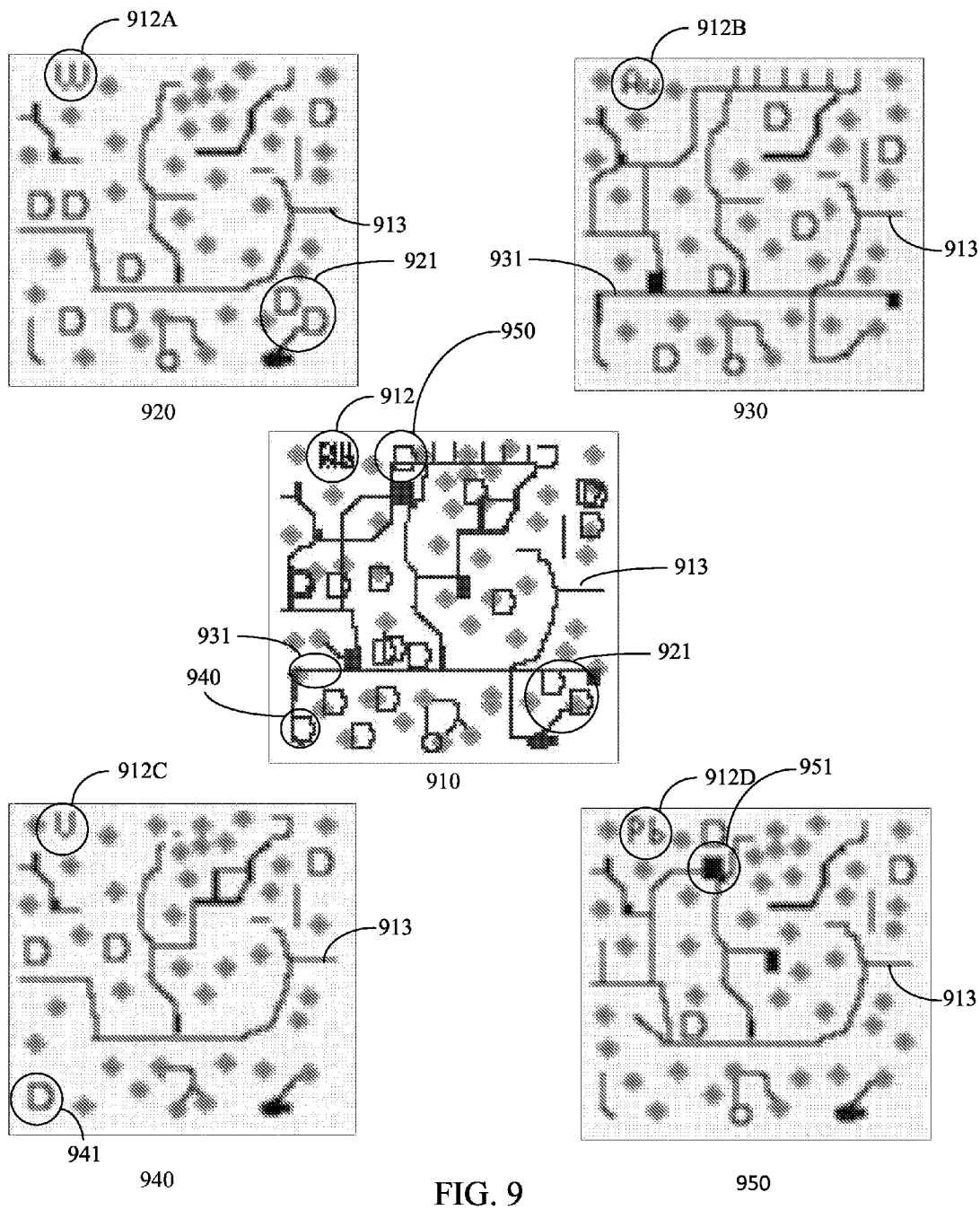
FIG. 9 is an illustration of a simulated sample made from structures having different sensitivities to the characteristic x-rays produced by different materials, and images of that sample taken with a patterned x-ray target made from different materials in accordance with an embodiment of the disclosure.

FIG. 9 is an illustration of a simulated sample made from structures having different sensitivities to the characteristic x-rays produced by different materials, and images of that sample taken with a patterned x-ray target made from different materials. The simulated sample 910 contained 10,000 pixels arranged in a 100×100 grid, where each pixel was assigned a uniform 5% x-ray absorption to represent a solid object. Various features, such as features 912, were added to the simulated sample 910 and given different x-ray absorptions and sensitivities to the characteristic x-rays produced by W, Au, V and Pb. The simulated sample 910 was subsequently imaged with x-rays from a simulated target patterned to contain sixteen 200 nm 4×4 Hadamard matrices. Four of the sixteen pixels in a given Hadamard matrix simulated the emission of x-rays characteristic of W, four simulated the emission of x-rays characteristic of Au, four simulated the emission of x-rays characteristic of V, and four simulated the emission of x-rays characteristic of Pb. Corresponding pixels in the remaining Hadamard matrices simulated the emission of the same W, Au, V and Pb characteristic x-rays. The x-ray absorption images obtained were inverse Hadamard transformed to obtain separate images for each of the sixteen pixels in the Hadamard matrices. The inverse Hadamard transformed images corresponding to the pixels simulating the emission of W, Au, V and Pb characteristic x-rays were separately combined to obtain an image 920 obtained from a simulated W target, an image 930 made from a simulated Au target, an image 940 made from a simulated V target, and an image 950 made from a simulated Pb target.

As shown in images 920-950, different features can be seen in the different images depending on the sensitivity of the different features to the characteristic x-rays of W, Au, V and Pb. Feature 912 in simulated sample 910 was created so that different parts of the feature 912 were sensitive to different characteristic x-rays of the x-ray producing materials. As a result, image 920 shows those portions 912A of feature 912 that were sensitive to W characteristic x-rays, image 930 shows those portions 912B of feature 912 that were sensitive to Au characteristic x-rays, image 940 shows those portions 912C of feature 912 that were sensitive to V characteristic x-rays, and image 950 shows those portions 912D of feature 912 that were sensitive to Pb characteristic x-rays.

Some of the features in the simulated sample 910, such as feature 913, were equally sensitive to the characteristic x-rays of all of the materials, and therefore identically appear in all of the images 920 through 950. By contrast, other features were only given sensitivity to the characteristic x-rays of a particular material, and therefore only appear in the images corresponding to that particular material. Thus, feature 921 which was only sensitive to W characteristic x-rays only appears in the image 920 corresponding to W, feature 931 which was only sensitive to Au characteristic x-rays only appears in image 930 corresponding to Au, feature 941 which was only sensitive to V characteristic x-rays only appears in image 940 corresponding to V, and feature 951 which was only sensitive to Pb characteristic x-rays only appears in image 950 corresponding to Pb.

Figure 10:
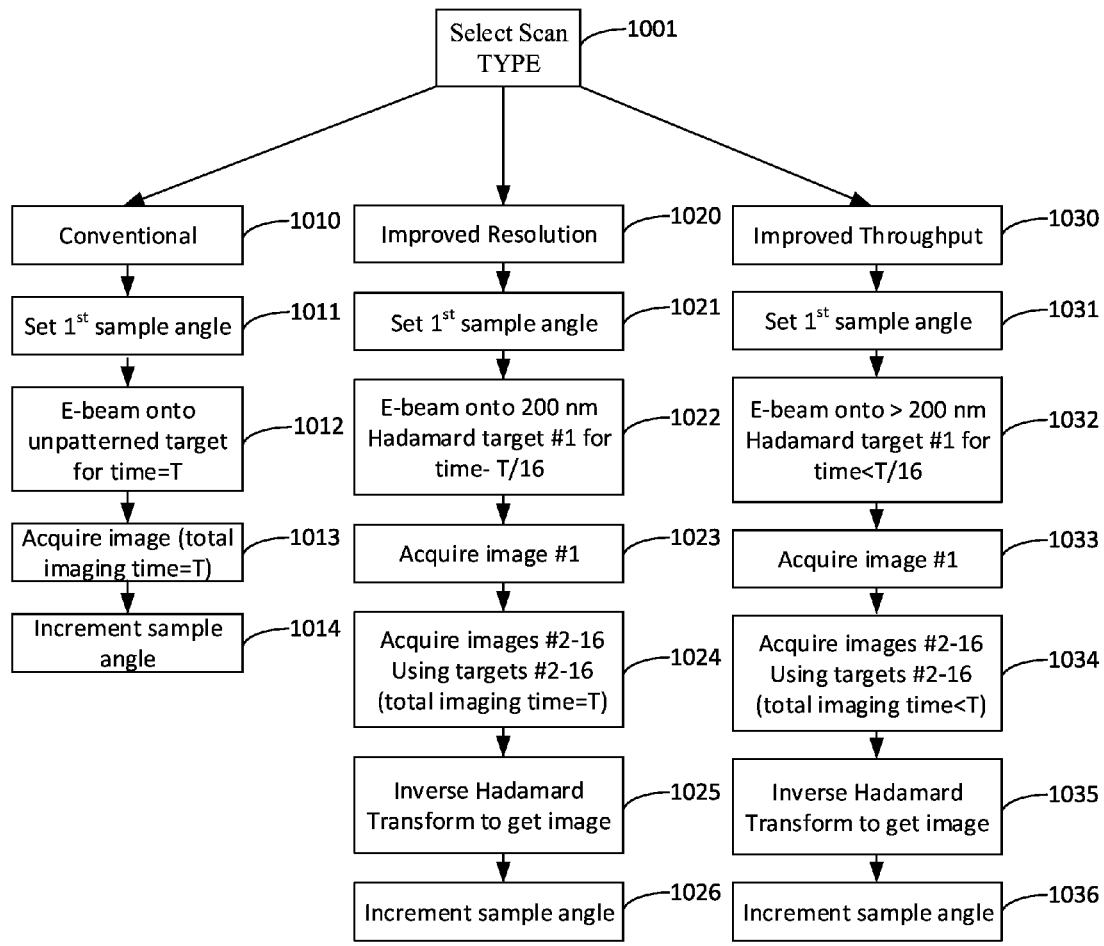
FIG. 10 is a flow chart depicting a method for collecting x-ray tomography data for a sample according to an embodiment of the disclosure.

FIG. 10 is a flow chart depicting a method for collecting x-ray tomography data for a sample. The method can be performed by the x-ray tomography system 200 shown in FIG. 2. Prior to beginning the scan, the target 210 and the sample 220 can be imaged by the focused electron beam 280 to identify and localize any target structures 212 or grids of target structures 212 in the target 210. The scan then begins by selecting a scan type 1001. Possible scan types are a conventional scan 1010, an improved resolution scan 1020 or an improved throughput scan 1030.

For conventional scans, the sample 220 is rotated to its first sample angle 1011. Next, the wide electron beam 290 is focused on a conventional un-patterned target for a predetermined period of time to generate a flux of x-rays to illuminate the sample 1012. For example, the wide electron beam 290 can be focused on any one of the un-patterned target structures 820 shown in FIG. 8, where the particular target structure 820 that is chosen can depend on the sensitivity of the sample to the characteristic x-rays produced by the material (e.g., V) from which the target structure 820 is made. The x-rays transmitted through the sample are collected by x-ray detector 230, and an x-ray absorption image is recorded 1013. The sample 220 is rotated to the next sample angle 1014, and the process is repeated until x-ray absorption images have been recorded for all desired sample angles, at which point tomography transforms can be performed to generate cross-sectional images of the sample 220 from the recorded absorption images.

For improved resolution scans 1020, the sample is again rotated to its first sample angle 1021. Next, the wide electron beam 290 is focused on a target patterned with x-ray producing structures 212 that form a first one of a plurality of orthogonal Hadamard matrix structures for a predetermined period of time to generate a patterned flux of x-rays to illuminate the sample 1022. The Hadamard matrix structure can be of any dimension N×N, and the predetermined period of time can be $1/N^2$ the period of time used in the conventional scan 1010. For example, the wide electron beam 290 can be focused on any one of the structures 830 shown in FIG. 8 that are patterned as Hadamard matrices. The particular Hadamard matrix structure chosen can depend on the sensitivity of the sample to the characteristic x-rays produced by the material used to make the structure, and the desired resolution. To achieve better resolution, a higher dimensioned Hadamard matrix structure (e.g., 4×4) can be chosen over a lower dimensioned Hadamard matrix structure (e.g., 2×2). In addition, the structures 212 used to form the Hadamard matrices can have smaller cross-sectional areas or characteristic widths.

The x-rays transmitted through the sample are collected by x-ray detector 230, and an image of the Hadamard transformed absorption image of the sample is recorded 1023. The illuminating electron beam 290, which may be a wide beam, is then sequentially stepped through the remaining Hadamard matrix structures (e.g., as shown in FIG. 4), focusing on each for the predetermined period of time, and the x-rays patterns thereby produced are used to illuminate the sample 220. The x-rays transmitted through the sample are collected by x-ray detector 230, and a plurality of Hadamard transformed absorption images are thereby recorded 1024. The plurality of Hadamard transformed absorption images are inverted using a plurality of inverse Hadamard transforms, and the inverted images are combined to obtain the absorption image of the sample at the first angle 1025. The sample 220 is then rotated to the next sample angle 1026, and the process is repeated until absorption images have been obtained for all desired sample angles, at which point tomography transforms can be performed to generate a cross-sectional image of the sample 220 from the absorption images.

For improved throughput scans 1030, the sample is again rotated to its first sample angle 1031, and the wide electron beam 290 is focused on a target patterned with x-ray producing structures 212 that form a first one of a plurality of orthogonal Hadamard matrix structures for a predetermined period of time 1032. As before, the Hadamard matrix structure can be of any dimension N×N, however for improved throughput scans, the predetermined period of time can be less than $1/N^2$ period of time used in the conventional scan 1010. For example, the wide electron beam 290 can be focused on any one of the structures 840 shown in FIG. 8 that are patterned as Hadamard matrices. As before, the particular Hadamard matrix structure chosen can depend on the sensitivity of the sample to the characteristic x-rays produced by the material used to make the structure, and the desired resolution. For higher throughput, lower dimensioned Hadamard matrices (e.g., 2×2) can be chosen over higher dimensioned Hadamard matrices (e.g., 4×4). In addition, the structures 212 used to form the Hadamard matrices can have larger cross-sectional areas or characteristic widths.

The x-rays transmitted through the sample are collected by x-ray detector 230, and an image of the Hadamard transformed absorption image of the sample is recorded 1033. The wide electron beam 290 is then sequentially stepped through the remaining Hadamard matrix target structures (e.g., as shown in FIG. 4), focusing on each for the predetermined period of time, and the x-rays patterns thereby produced are used to illuminate the sample 220. The x-rays transmitted through the sample are collected by x-ray detector 230, and a plurality of Hadamard transformed absorption images are thereby recorded 1034. The plurality of Hadamard transform absorption images are inverted using a plurality of inverse Hadamard transforms, and the inverted images are combined to obtain the absorption image of the sample at the first angle 1035. The sample 220 is rotated to the next sample angle 1036, and the process is repeated at that and subsequent sample angles until absorption spectra have been obtained for all sample angles, at which point tomography transforms can be performed to generate cross-sectional images of the sample 220 from the absorption images.

An SEM minicolumn (FIG. 11) was developed to produce beams with energies of up to 60 keV, currents of at least 30 nA, diameters of less than 10 nm, and fields-of-view (FoVs) of more than 1.0 mm. The specific beam diameters and currents are determined by the SEM minicolumn's beam-defining aperture (BDA). Different tradeoffs between resolution and current may be achieved with larger or smaller BDAs. The SEM minicolumn may be configured with a single fixed BDA, or alternatively with a movable BDA assembly to allow the SEM minicolumn to have multiple, selectable resolution/current settings. The SEM minicolumn shown in FIG. 11 can be employed as the SEM column 260 shown in FIG. 2, however, other SEM columns or minicolumns can be employed as the SEM column 260. As such, many of the processes discussed above, e.g., illuminating one or more high aspect ratio structures made from different materials, having different cross-sectional areas, or arranged in different patterns or sequences such as a plurality of Hadamard matrices, can be performed by employing one or more standard SEM columns or minicolumns, and do not require the use of the SEM minicolumn shown in FIG. 11.

Figure 11:
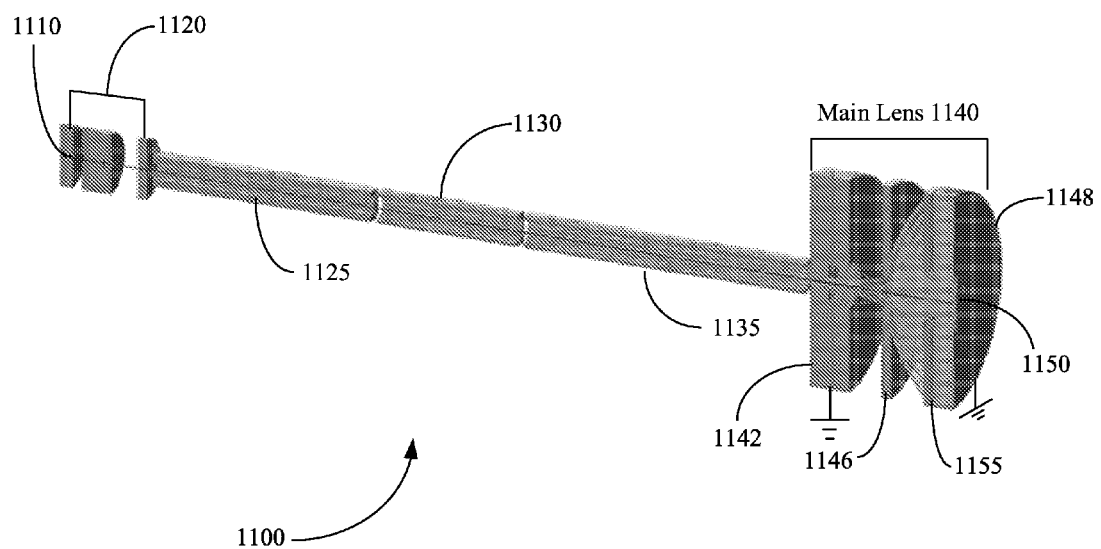
FIG. 11 shows an isometric cross-sectional view of an SEM minicolumn according to an embodiment of the disclosure.

When used as the SEM column 260 shown in FIG. 2, the SEM minicolumn shown in FIG. 11 can be operated in SEM mode to generate a focused electron beam 280 (<10 nm wide) to obtain high resolution images of both the sample 220 and x-ray target 210 with back-scattered electron (BSE) imaging. The SEM minicolumn can also be operated in a NanoCT mode to generate a wide electron beam 290 (>200 nm wide) that can be stepped through the field-of-view to separately illuminate any one of a plurality of x-ray producing target structures 212. To image the target 210 or sample 220 in SEM mode, a BSE detector is configured to efficiently collect backscattered electrons (BSEs) down to a substantial energy loss (~47 keV) from the primary beam (~60 keV). The BSE detector can be radially segmented to measure the energy distribution of the back scattered electrons, and azimuthally segmented to capture topographic information about the target 210 or sample 220.

FIG. 11 shows an isometric cross-sectional view of the SEM minicolumn. The SEM minicolumn 1100 consists of a standard Schottky electron source 1110. Emitted electrons are accelerated to high energy (e.g., 60 keV) and into a nearly parallel beam by a gun lens 1120. The high energy beam enters a beam blanker 1125 that deflects the beam off-axis. The beam blanker 1125 can either consist of parallel plate electrodes or quadrupole electrodes. A pair of beam deflectors 1130, 1135, typically consist of a pair of electrostatic octupoles, subsequently directs the beam into the main lens 1140. The main lens 1140 contains three electrodes: a center focusing electrode 1146 at a high negative voltage (e.g., −52 kV), and two outer electrodes 1142, 1148 at ground, and focuses the beam onto a sample 1150. To minimize beam broadening at the sample due to electron-electron interactions, the SEM minicolumn 1100 is kept as short as possible. In addition, no beam crossovers are typically employed. In one embodiment, SEM minicolumn 1100 measures 150 mm from the Schottky emitter 1110 to the sample 1150. For stable high voltage operation, all electric fields between lens and deflector electrodes are kept below 10 kV/mm.

The SEM minicolumn 1100 can produce a 60 keV beam with an on-axis beam diameter of 5.9 nm (FWHM). When the beam is scanned across its field-of-view, several off-axis beam aberrations are dynamically corrected to minimize the off-axis beam diameter. Coma, which results in a radial blurring of the beam, is corrected by adjusting the ratio of the strengths of the upper and lower deflectors 1130, 1135 to control the angle and radial position of the beam as it enters the main lens 1140. Curvature of field, which results in a circular blurring of the beam, is corrected by changing the voltage on focusing electrode 1146 of the main lens 1140. Astigmatism, which results in the formation of two beam "foci" above and below the sample plane, is corrected by adding a quadrupole electrostatic excitation to the octupole deflection electrodes 1130, 1135 in addition to the normal dipole excitation used to deflect the beam. And distortion, which results in the beam landing on the wrong place on the sample, is corrected by adding a small cubically-varying component to the normally linearly-varying voltages applied to the deflection electrodes 1130, 1135.

These dynamic corrections can preserve the on-axis beam profile out to more than 200 µm off-axis. At 500 µm off-axis, the beam profile becomes somewhat elongated in a direction that is parallel to the deflection axis, while at 600 µm off-axis, the beam profile becomes somewhat pear-shaped. However, even at 600 µm off-axis, the effects of the beam profile on the acquired images are minimal, thus SEM minicolumn 1100 has a fairly large usable field-of-view.

Figure 12:
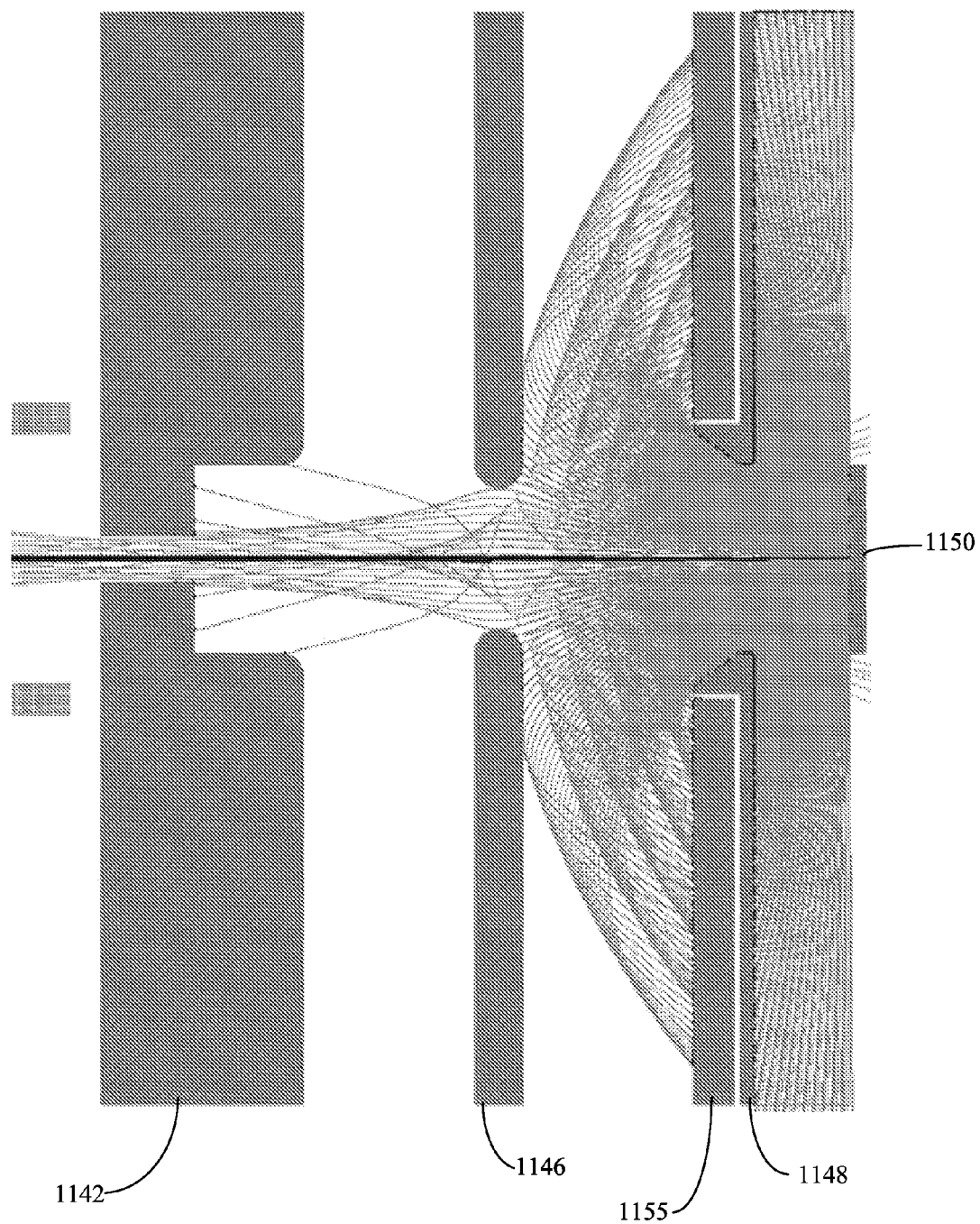
FIG. 12 shows a close-up cross-sectional view of the main lens of the SEM minicolumn of FIG. 11.

FIG. 12 shows a close-up cross-sectional view of the main lens of the SEM minicolumn. As shown in FIG. 12, a BSE detector 1155 is integrated with the third electrode 1148 of the main lens 1150. Back scattered electrons (BSEs) emitted from the sample 1150 due to bombardment by the primary beam emerge upwards from the sample surface into a full 2π steradian solid angle. BSEs that leave the sample at small angles relative to the sample surface (e.g., <~55°) strike the bottom of grounded third electrode 1148 and are not detected. BSEs that leave the sample at large angles relative to the sample surface (e.g., >~80°) pass through the bores in the third electrode 1148 and focusing electrode 1146 and strike the bottom of the grounded first electrode 1142 and are also not detected. BSEs that leave the sample within the angular range of ~55° to ~80° pass through the bore in the third electrode 1148, and are radially deflected by the electric field between the focusing electrode 1146 and the third electrode 1148, as shown.

BSEs that have lost substantial amounts of energy in the sample are deflected more, and strike the BSE detector 1155 nearer the optical axis of the main lens 1140. BSEs that have lost minimal energy in the sample are deflected less, and strike the BSE detector further from the optical axis as shown. With a radially segmented BSE detector 1155, these differences in BSE landing locations allow for measurement and analysis of the BSE energy distribution, and elemental analysis into the composition of the sample. Moreover, an azimuthally segmented BSE detector would allow for measurement and analysis of the distribution of the azimuthal component of the BSE scattering angle, which remains constant over the BSE trajectories between the sample 1150 and BSE detector 1155 due to the azimuthal symmetry of the main lens 1140. Analysis of such a distribution can provide topographic information about the sample, which affects the BSE scattering angle distribution.

Figure 13:
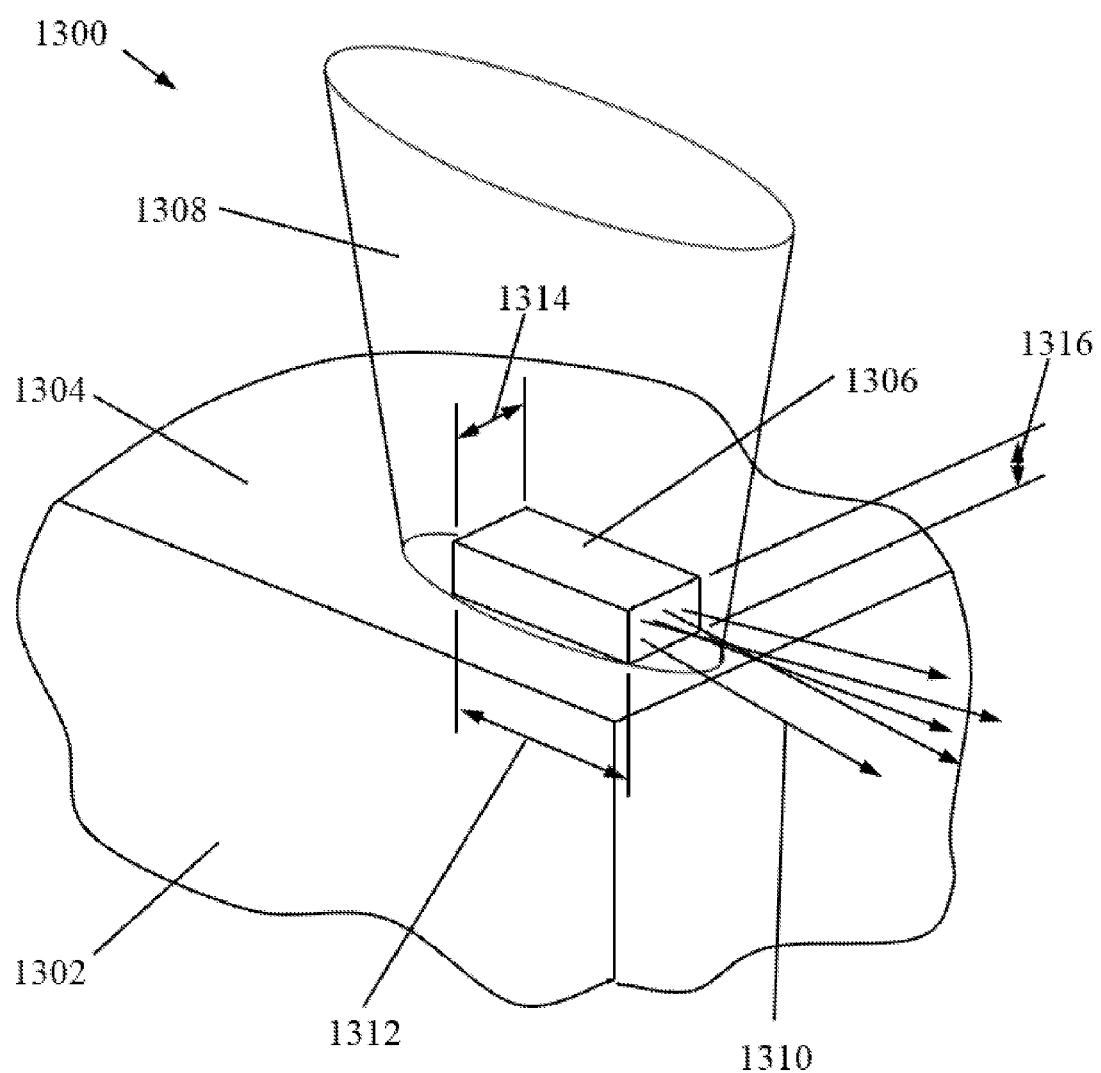
FIG. 13 shows an x-ray producing structure in an electron beam target according to an embodiment of the disclosure.

FIG. 13 shows an x-ray producing structure 1306 in an electron beam target 1300 according to an embodiment of the disclosure. Structure 1306 has been fabricated on the surface 1304 of a substrate 1302. To generate x-rays, an electron beam 1308 is directed onto structure 1306 as shown, resulting in the emission of x-rays into a full 4π steradians (i.e., into all directions). X-rays 1310 represent the portion of the overall x-ray emission which is directed towards a sample (not shown). The dimensions 1314 and 1316 of structure 1306 determine the effective source size from the perspective of the sample which would be located to the lower right of structure 1306, along the directions of x-rays 1310. The dimension 1312 of structure 1306 determines the total x-ray flux 1310 generated when e-beam 1308 is directed towards structure 1306. Although the area of e-beam 1308 is larger than the area (dimension 1314×dimension 1312) of structure 1306, as seen from the source of the e-beam 1308 (not shown), the source size is not determined by the e-beam area, but only by the area (dimension 1314×dimension 1316) of structure 1306 as "seen" by the sample.

Figure 14:
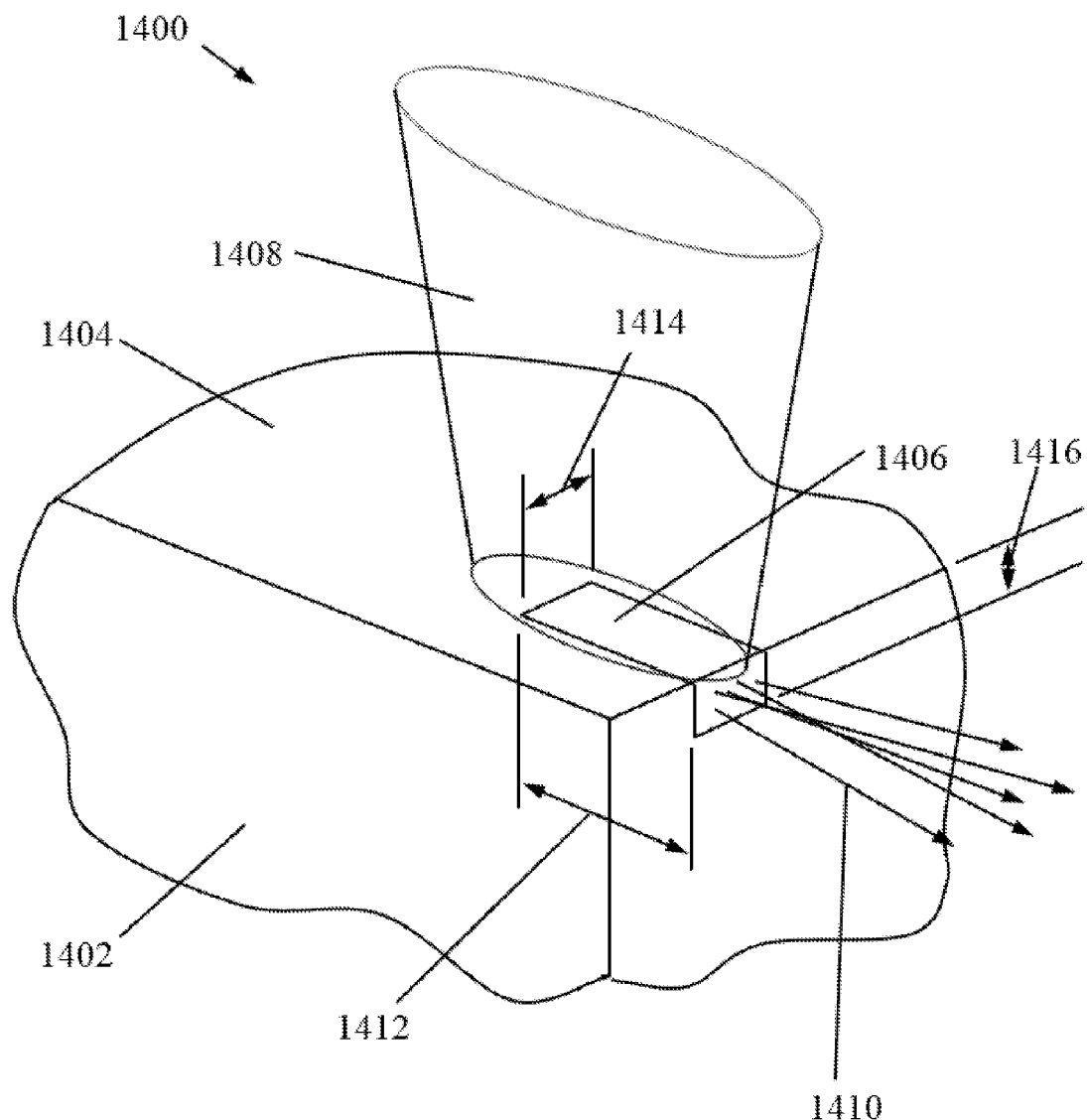
FIG. 14 shows an x-ray producing structure in an electron beam target according to an embodiment of the disclosure.

FIG. 14 shows an x-ray producing structure 1406 in an electron beam target 1400 according to an embodiment of the disclosure. Structure 1406 has been fabricated below the surface 1404 of a substrate 1402—this patterning of structure 1406 may be effected using well-known "Damascene" methods from the semiconductor industry. To generate x-rays, an electron beam 1408 is directed onto structure 1406 as shown, resulting in the emission of x-rays into a full 4 π steradians (i.e., into all directions). X-rays 1410 represent the portion of the overall x-ray emission which is directed towards a sample (not shown). The dimensions 1414 and 1416 of structure 1406 determine the effective source size from the perspective of the sample, which would be located to the lower right of structure 1406, along the directions of x-rays 1410. The dimension 1412 of structure 1406 determines the total x-ray flux 1410 generated when e-beam 1408 is directed towards structure 1406. Although the area of e-beam 1408 is larger than the area (dimension 1414×dimension 1412) of structure 1406 as seen from the source of the e-beam 1408 (not shown), the source size is not determined by the e-beam area, but only by the area (dimension 1414×dimension 1416) of structure 1406 as "seen" by the sample.

Figure 15:
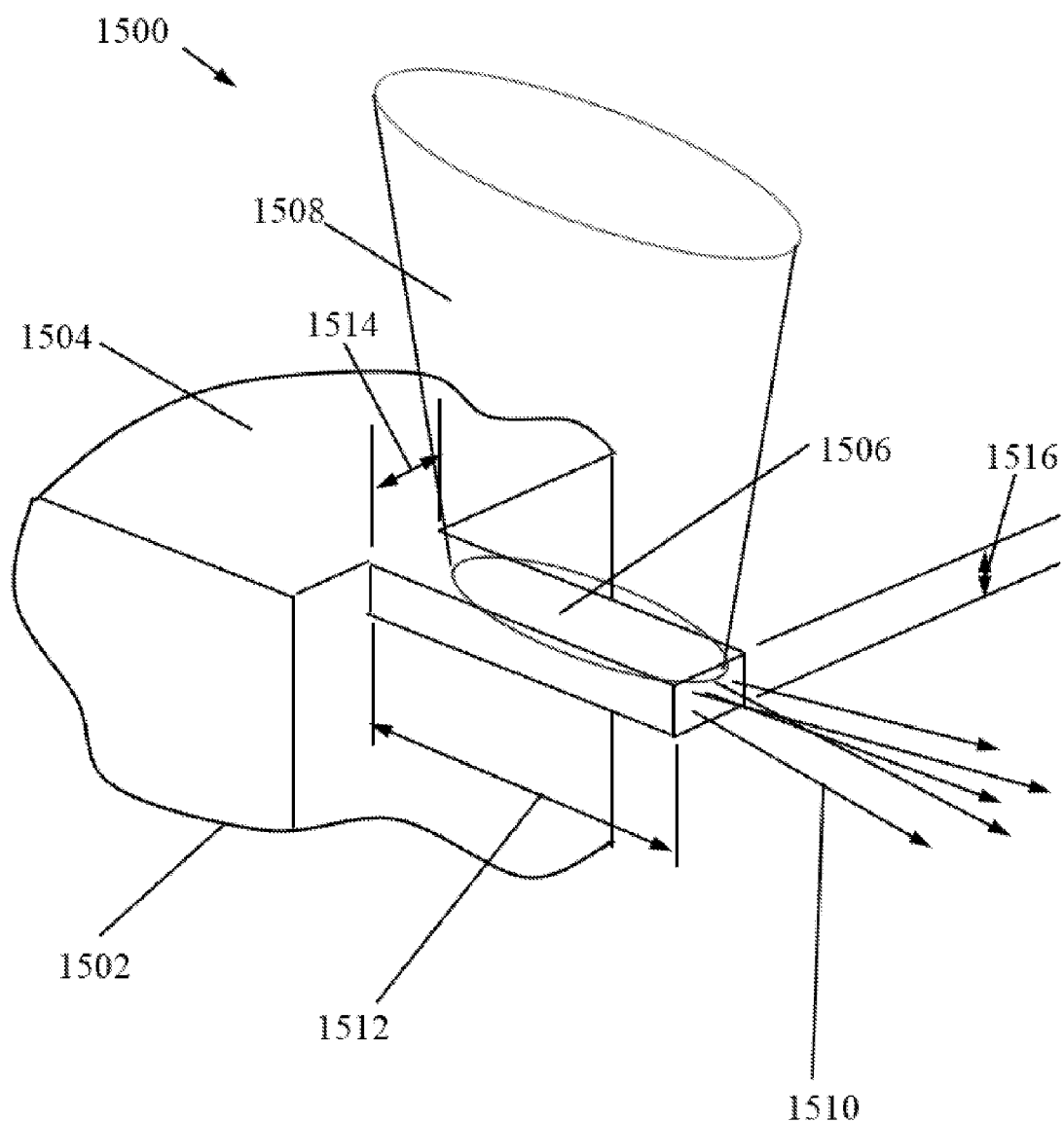
FIG. 15 shows an x-ray producing structure in an electron beam target according to an embodiment of the disclosure.

FIG. 15 shows an x-ray producing structure 1506 in an electron beam target 1500 according to an embodiment of the disclosure. Structure 1506 has been fabricated as a structure cantilevered outwards from a substrate 1502, parallel with a surface 1504—this patterning of structure 1506 may be effected focused ion beam milling or other three-dimensional patterning methods. To generate x-rays, an electron beam 1508 is directed onto structure 1506 as shown, resulting in the emission of x-rays into a full 4π steradians (i.e., into all directions). X-rays 1510 represent the portion of the overall x-ray emission which is directed towards a sample (not shown). The dimensions 1514 and 1516 of structure 1506 determine the effective source size from the perspective of the sample, which would be located to the lower right of structure 1506, along the directions of x-rays 1510. The dimension 1512 of structure 1506 determines the total x-ray flux 1510 generated when e-beam 1508 is directed towards structure 1506. Although the area of e-beam 1508 is larger than the area (dimension 1514×dimension 1512) of structure 1506 as seen from the source of the e-beam 1508 (not shown), the source size is not determined by the e-beam area, but only by the area (dimension 1514×dimension 1516) of structure 1506 as "seen" by the sample.

The following are additional enumerated embodiments according to the present disclosure:

A first embodiment, which is an x-ray target that includes a substrate made from a soft x-ray producing material, and a high aspect ratio structure made from a hard x-ray producing material. The hard x-ray producing material is embedded in the substrate, formed on the substrate, cantilevered out from the edge of the substrate, or any combination thereof. The high aspect ratio structure comprises a plurality of high aspect ratio structures arranged in one or more grids or arrays, and the high aspect ratio structures in one of the one or more grids or arrays are arranged to form a Hadamard matrix structure.

A second embodiment, which is the x-ray target of the first embodiment, wherein the high aspect ratio structure includes at least two high aspect ratio structures having different cross-sectional areas.

A third embodiment, which is the x-ray target of any of the first through second embodiments, wherein the high aspect ratio structure includes at least two high aspect ratio structures made from different hard x-ray producing materials.

A fourth embodiment, which is the x-ray target of any of the first through third embodiments, wherein the high aspect ratio structure includes a plurality of high aspect ratio structures arranged in one or more grids or arrays.

A fifth embodiment, which is the x-ray target of the fourth embodiment, wherein the one or more grids or arrays include one or more irregular grids or arrays.

A sixth embodiment, which is the x-ray target of the fourth embodiment, wherein the high aspect ratio structures in one of the one or more grids or arrays are arranged to form a Hadamard matrix structure.

A seventh embodiment, which is the x-ray target of the fourth embodiment, wherein the plurality of high aspect ratio structures in the one or more grids or arrays are arranged to form a plurality of Hadamard matrix structures, each of the plurality of Hadamard matrix structures being a member of a set of orthogonal Hadamard matrix structures.

A eighth embodiment, which is the x-ray target of the seventh embodiment, wherein at least two of the high aspect ratio structures in each of the plurality of Hadamard matrix structures are made from different hard x-ray producing materials, such that the spatial distribution of the at least two high aspect ratio structures made from the different hard x-ray producing materials is the same in each of the plurality of Hadamard matrix structures.

A ninth embodiment, which is the x-ray target of the fourth embodiment, wherein the plurality of high aspect ratio structures in the one or more grids or arrays are arranged to form a plurality of sets of orthogonal Hadamard matrix structures, each set of the plurality of sets of orthogonal Hadamard matrix structures containing a plurality of orthogonal Hadamard matrix structures.

A tenth embodiment, which is the x-ray target of the ninth embodiment, wherein the plurality of orthogonal Hadamard matrix structures in at least two sets of the plurality of sets of orthogonal Hadamard matrix structures are made from high aspect ratio structures made from different hard x-ray producing materials.

A eleventh embodiment, which is the x-ray target of the ninth embodiment, wherein the plurality of orthogonal Hadamard matrix structures in at least two sets of the plurality of sets of orthogonal Hadamard matrix structures are made from high aspect ratio structures having different cross-sectional areas.

A twelfth embodiment, which is the x-ray target of the ninth embodiment, wherein at least two of the high aspect ratio structures in each of the plurality of orthogonal Hadamard matrix structures in at least one set of the plurality of sets of orthogonal Hadamard matrix structures are made from different hard x-ray producing materials, such that the spatial distribution of the at least two high aspect ratio structures made from the different hard x-ray producing materials is the same in each of the plurality of orthogonal Hadamard matrix structures in the at least one set of the plurality of sets of orthogonal Hadamard matrix structures.

A thirteenth embodiment, which is the x-ray target of the ninth embodiment, wherein at least two of the high aspect ratio structures in each of the plurality of orthogonal Hadamard matrix structures in at least one set of the plurality of sets of orthogonal Hadamard matrix structures are made from high aspect ratio structures having different cross-sectional areas.

A fourteenth embodiment, which is the x-ray target of any of the first through thirteenth embodiments, wherein the high aspect ratio structure is embedded in or formed on a thinned portion of the substrate.

A fifteenth embodiment, which is a method for generating an x-ray image of a sample, the method including:

sequentially focusing an electron beam on each of a plurality of orthogonal Hadamard matrix structures, each orthogonal Hadamard matrix structure made from a plurality of high aspect ratio structures arranged at different pixel locations in a pixilated grid pattern, each high aspect ratio structure made from a hard x-ray producing material;

illuminating the sample with x-rays produced by sequentially focusing the electron beam on each of the plurality of orthogonal Hadamard matrix structures;

sequentially detecting the x-rays transmitted through the sample, and recording the detected x-rays in a plurality of Hadamard transformed x-ray images;

applying one or more inverse Hadamard transforms to the plurality of Hadamard transformed x-ray images to generate one or more x-ray images, wherein each of the one or more x-ray images is generated from an inverse Hadamard transform corresponding to a different pixel in the pixilated grid of high aspect ratio structures that make up the orthogonal Hadamard matrix structures; and combining the one or more x-ray images to generate an x-ray image of the sample.

A sixteenth embodiment, which is the method of the fifteenth embodiment, wherein each of the orthogonal Hadamard matrix structures is located at a different location on the same x-ray target.

A seventeenth embodiment, which is the method of the sixteenth embodiment, further including determining the location of each of the plurality of orthogonal Hadamard matrix structures on the x-ray target before sequentially focusing the electron beam on each of the plurality of orthogonal Hadamard matrix structures.

A eighteenth embodiment, which is the method of the sixteenth embodiment, wherein applying the one or more inverse Hadamard transforms includes correcting for relative parallax in each of the Hadamard transformed x-ray images due to the different locations of the orthogonal Hadamard matrix structures on the x-ray target.

A nineteenth embodiment, which is the method of the eighteenth embodiment, wherein combining the x-ray images includes correcting for relative parallax in each of the x-ray images due to the different pixel locations of the high aspect ratio structures in each of the orthogonal Hadamard matrix structures.

A twentieth embodiment, which is the method of any of the fifteenth through nineteenth embodiments, wherein at least two high aspect ratio structures in each of the plurality of orthogonal Hadamard matrix structures are made from different hard x-ray producing materials, such that the spatial distribution of the at least two high aspect ratio structures made from the different hard x-ray producing materials is the same in each of the plurality of orthogonal Hadamard matrix structures.

A twenty-first embodiment, which is the method of the twentieth embodiment, wherein combining the one or more x-ray images includes combining x-ray images corresponding to pixels in the orthogonal Hadamard matrix structures having high aspect ratio structures made from the same hard x-ray producing material.

A twenty-second embodiment, which is the method of any of the fifteenth through twenty-first embodiments, wherein applying one or more inverse Hadamard transforms to the plurality of Hadamard transformed x-ray images to generate one or more x-ray images includes adding or subtracting the plurality of Hadamard transformed x-ray images based on a Hadamard code.

A twenty-third embodiment, which is the method of any of the fifteenth through twenty-second embodiments, wherein the plurality of orthogonal Hadamard matrix structures are made from a plurality of high aspect ratio structures made from a first hard x-ray producing material, further including:

sequentially focusing the electron beam on each of a second plurality of orthogonal Hadamard matrix structures, each made from a plurality of high aspect ratio structures made from a second hard x-ray producing material;

illuminating the sample with the x-rays produced by sequentially focusing the electron beam on each of the second plurality of orthogonal Hadamard matrix structures;

sequentially detecting the x-rays transmitted through the sample, and recording the detected x-rays in a second plurality of Hadamard transformed x-ray images;

applying one or more inverse Hadamard transforms to the second plurality of Hadamard transformed x-ray images to generate one or more x-ray images for the second hard x-ray producing material, wherein each of the one or more x-ray images for the second hard x-ray producing material is generated from an inverse Hadamard transform corresponding to a different pixel; and combining the one or more x-ray images for the second hard x-ray producing material to generate an x-ray image of the sample for the second material.

A twenty-fourth embodiment, which is the method of any of the fifteenth through twenty-third embodiments, wherein the plurality of orthogonal Hadamard matrix structures are made from a plurality of high aspect ratio structures having a first cross sectional area, further including:

focusing the electron beam on each of a second plurality of orthogonal Hadamard matrix structures, each made from a plurality of high aspect ratio structures having a second cross-sectional area;

illuminating the sample with the x-rays produced by sequentially focusing the electron beam on each of the second plurality of orthogonal Hadamard matrix structures;

sequentially detecting the x-rays transmitted through the sample, and recording the detected x-rays in a second plurality of Hadamard transformed x-ray images;

applying one or more inverse Hadamard transforms to the second plurality of Hadamard transformed x-ray images to generate one or more higher resolution x-ray images, wherein each of the one or more higher resolution x-ray images is generated from an inverse Hadamard transform corresponding to a different pixel; and combining the one or more higher resolution x-ray images to generate a higher resolution x-ray image of the sample.

A twenty-fifth embodiment, which is a computer program product, embedded on a non-transitory medium, that includes instructions operable to cause a programmable processor to:

sequentially focus an electron beam on each of a plurality of orthogonal Hadamard matrix structures, each orthogonal Hadamard matrix structure made from a plurality of high aspect ratio structures arranged at different pixel locations in a pixilated grid pattern, each high aspect ratio structure made from a hard x-ray producing material;

sequentially detect x-rays produced by the plurality of orthogonal Hadamard matrix structures and transmitted through the sample, and record the detected x-rays in a plurality of Hadamard transformed x-ray images;

apply one or more inverse Hadamard transforms to the plurality of Hadamard transformed x-ray images to generate one or more x-ray images, wherein each of the one or more x-ray images is generated from an inverse Hadamard transform corresponding to a different pixel in the pixilated grid of high aspect ratio structures that make up the orthogonal Hadamard matrix structures; and combine the one or more x-ray images to generate an x-ray image of the sample.

A twenty-sixth embodiment, which is the computer program product of the twenty-fifth embodiment, wherein each of the orthogonal Hadamard matrix structures is located at a different location on the same x-ray target.

A twenty-seventh embodiment, which is the computer program product of the twenty-sixth embodiment, further including instructions operable to cause the programmable processor to determine the location of each of the plurality of orthogonal Hadamard matrix structures on the x-ray target before sequentially focusing the electron beam on each of the plurality of orthogonal Hadamard matrix structures.

A twenty-eighth embodiment, which is the computer program product of the twenty-sixth embodiment, wherein the instructions to apply the one or more inverse Hadamard transforms include instructions to correct for relative parallax in each of the Hadamard transformed x-ray images due to the different locations of the orthogonal Hadamard matrix structures on the x-ray target.

A twenty-ninth embodiment, which is the computer program product of the twenty-eighth embodiment, wherein the instructions to combine the x-ray images include instructions to correct for relative parallax in each of the x-ray images due to the different pixel locations of the high aspect ratio structures in each of the orthogonal Hadamard matrix structures.

A thirtieth embodiment, which is the computer program product of any of the twenty-fifth through twenty-ninth embodiments, wherein at least two high aspect ratio structures in each of the plurality of orthogonal Hadamard matrix structures are made from different hard x-ray producing materials, such that the spatial distribution of the at least two high aspect ratio structures made from the different hard x-ray producing materials is the same in each of the plurality of orthogonal Hadamard matrix structures.

A thirty-first embodiment, which is the computer program product of the thirtieth embodiment, wherein the instructions to combine the one or more x-ray images include instructions to combine x-ray images corresponding to pixels in the orthogonal Hadamard matrix structures having high aspect ratio structures made from the same hard x-ray producing material.

A thirty-second embodiment, which is the computer program product of any of the twenty-fifth through thirty-first embodiments, wherein the instructions to apply one or more inverse Hadamard transforms to the plurality of Hadamard transformed x-ray images to generate one or more x-ray images include the instructions to add or subtract the plurality of Hadamard transformed x-ray images based on a Hadamard code.

A thirty-third embodiment, which is the computer program product of any of the twenty-fifth through thirty-second embodiments, wherein the plurality of orthogonal Hadamard matrix structures are made from a plurality of high aspect ratio structures made from a first hard x-ray producing material, further including instructions operable to cause the programmable processor to:

sequentially focus the electron beam on each of a second plurality of orthogonal Hadamard matrix structures, each made from a plurality of high aspect ratio structures made from a second hard x-ray producing material;

sequentially detect the x-rays produced by each of the second plurality of orthogonal Hadamard matrix structures and transmitted through the sample, and record the detected x-rays in a second plurality of Hadamard transformed x-ray images;

apply one or more inverse Hadamard transforms to the second plurality of Hadamard transformed x-ray images to generate one or more x-ray images for the second hard x-ray producing material, wherein each of the one or more x-ray images for the second hard x-ray producing material is generated from an inverse Hadamard transform corresponding to a different pixel; and combine the one or more x-ray images for the second hard x-ray producing material to generate an x-ray image of the sample for the second hard x-ray producing material.

A thirty-fourth embodiment, which is the computer program product of any of the twenty-fifth through thirty-third embodiments, wherein the plurality of orthogonal Hadamard matrix structures are made from a plurality of high aspect ratio structures having a first cross sectional area, further including instructions operable to cause the programmable processor to:

sequentially focus the electron beam on each of a second plurality of orthogonal Hadamard matrix structures, each made from a plurality of high aspect ratio structures having a second cross-sectional area;

sequentially detect the x-rays produced by the second plurality of orthogonal Hadamard matrix structures and transmitted through the sample, and record the detected x-rays in a second plurality of Hadamard transformed x-ray images;

apply one or more inverse Hadamard transforms to the second plurality of Hadamard transformed x-ray images to generate one or more higher resolution x-ray images, wherein each of the one or more higher resolution x-ray images is generated from an inverse Hadamard transform corresponding to a different pixel; and combine the one or more higher resolution x-ray images to generate a higher resolution x-ray image of the sample.

A thirty-fifth embodiment, which is a method for generating an x-ray image of a sample, the method including:

raster scanning the sample with a focused electron beam to image the sample;

raster scanning an x-ray target with the focused electron beam to image the x-ray target and to locate a plurality of hard x-ray producing structures located on or embedded within the x-ray target;

illuminating one or more of the plurality of hard x-ray producing structures with an electron beam to generate a flux of x-rays;

detecting x-rays that pass through the sample at an x-ray detector; and recording an x-ray image of the sample from the detected x-rays.

A thirty-sixth embodiment, which is the method of the thirty-fifth embodiment, wherein illuminating one or more of the plurality of hard x-ray producing structures with an electron beam includes illuminating one of the plurality of hard x-ray producing structures with the focused electron beam.

A thirty-seventh embodiment, which is the method of any of the thirty-fifth through thirty-sixth embodiments, wherein illuminating one or more of the plurality of hard x-ray producing structures with an electron beam includes sequentially illuminating a plurality of identical hard x-ray producing structures with the focused electron beam.

A thirty-eighth embodiment, which is the method of any of the thirty-fifth through thirty-seventh embodiments, wherein illuminating one or more of the plurality of hard x-ray producing structures with an electron beam includes simultaneously illuminating a plurality of the hard x-ray producing structures with a wide electron beam.

A thirty-ninth embodiment, which is the method of the thirty-sixth embodiment, wherein at least two of the plurality of hard x-ray producing structures have different areas, and illuminating one of the plurality of hard x-ray producing structures with the focused electron beam includes illuminating a hard x-ray producing structure having a first area.

A fortieth embodiment, which is the method of the thirty-ninth embodiment, further including illuminating a hard x-ray producing structure having a second area, detecting x-rays that pass through the sample at the x-ray detector, and recording a second x-ray image of the sample from the detected x-rays.

A forty-first embodiment, which is the method of the fortieth embodiment, wherein the second area is smaller than the first area and the second x-ray absorption image has greater resolution.

A forty-second embodiment, which is the method of the thirty-sixth embodiment, wherein at least two of the plurality of hard x-ray producing structures are made from different materials, and illuminating one of the plurality of hard x-ray producing structures with the focused electron beam includes illuminating a hard x-ray producing structure made from a first material.

A forty-third embodiment, which is the method of the forty-second embodiment, further including: illuminating a hard x-ray producing structure made from a second material, detecting x-rays that pass through the sample at the x-ray detector, and recording a second x-ray image of the sample.

A forty-fourth embodiment, which is the method of the thirty-eighth embodiment, wherein a first plurality of the hard x-ray producing structures has a first area and a second plurality of the hard x-ray producing structures has a second area, and illuminating a plurality of the hard x-ray producing structures with the wide electron beam includes illuminating the first plurality of hard x-ray producing structures having the first area.

A forty-fifth embodiment, which is the method of the forty-fourth embodiment, further including illuminating the second plurality of hard x-ray producing structures having the second area, detecting x-rays that pass through the sample at the x-ray detector, and recording a second x-ray image of the sample.

A forty-sixth embodiment, which is the method of the forty-fifth embodiment, wherein the second area is smaller than the first area and the second x-ray absorption image has greater resolution.

A forty-seventh embodiment, which is the method of the thirty-eighth embodiment, wherein a first plurality of the hard x-ray producing structures are made from a first material and a second plurality of the hard x-ray producing structures are made from a second material, and illuminating a plurality of the hard x-ray producing structures with the wide electron beam includes illuminating the first plurality of hard x-ray producing structures made from the first material.

A forty-eighth embodiment, which is the method of the forty-seventh embodiment, further including illuminating the second plurality of hard x-ray producing structures made from the second material, detecting x-rays that pass through the sample at the x-ray detector, and recording a second x-ray image of the sample.

A forty-ninth embodiment, which is the method of the forty-fourth embodiment, wherein the first and second plurality of hard x-ray producing structures are respectively patterned to form Hadamard matrix structures.

A fiftieth embodiment, which is the method of the forty-seventh embodiment, wherein the first and second plurality of hard x-ray producing structures are respectively patterned to form Hadamard matrix structures.

A fifty-first embodiment, which is an x-ray projection system that includes a planar x-ray target, a sample holder, and a planar x-ray detector, wherein the plane of the planar x-ray detector is substantially parallel to the plane of the planar x-ray target, and where the planar x-ray target, the sample holder and the planar x-ray detector are substantially aligned along an axis that is substantially perpendicular to the plane of the x-ray target.

A fifty-second embodiment, which is the x-ray projection system of the fifty-first embodiment, further including a filter between the planar x-ray target and the planar x-ray detector to filter out soft x-rays.

A fifty-third embodiment, which is the x-ray projection system of any of the fifty-first through fifty-second embodiments, wherein the planar x-ray detector has a higher sensitivity for hard x-rays than for soft x-rays.

A fifty-fourth embodiment, which is the x-ray projection system of any of the fifty-first through fifty-third embodiments, further including a scanning electron microscope (SEM) column having an optical axis that is oblique to the axis of the planar x-ray target, the sample holder and the planar x-ray detector.

A fifty-fifth embodiment, which is the x-ray projection system of the fifty-fourth embodiment, wherein the SEM column is configured to illuminate the sample and at least a portion of the x-ray target with a focused electron beam.

A fifty-sixth embodiment, which is the x-ray projection system of the fifty-fourth embodiment, wherein the SEM column is configured to illuminate at least a portion of the x-ray target with a wide electron beam.

A fifty-seventh embodiment, which is the x-ray projection system of the fifty-fourth embodiment, wherein the SEM column includes a main lens that includes first, second and third electrodes having holes bored therein to permit the passage of an electron beam, wherein the first and third electrodes are substantially at ground, and the second electrode is at a large negative potential relative to ground.

A fifty-eighth embodiment, which is the x-ray projection system of the fifty-seventh embodiment, further including a back scattered electron (BSE) detector having a hole bored therein and seated between the second and third electrodes, the BSE detector substantially at ground.

A fifty-ninth embodiment, which is the x-ray projection system of the fifty-eighth embodiment, wherein the BSE detector is radially segmented.

A sixtieth embodiment, which is the x-ray projection system of the fifty-eighth embodiment, wherein the BSE detector is azimuthally segmented.

A sixty-first embodiment, which is the x-ray projection system of any of the fifty-seventh embodiment, wherein the potential on the second electrode is varied when the electron beam is deflected off axis to correct a curvature of field aberration.

A sixty-second embodiment, which is the x-ray projection system of the fifty-seventh embodiment, wherein the SEM column includes a pair of octupole electrodes for deflecting the electron beam into the main lens.

A sixty-third embodiment, which is the x-ray projection system of the sixty-second embodiment, wherein the relative strengths of the pair of octupole electrodes is set to correct for coma.

A sixty-fourth embodiment, which is the x-ray projection system of the sixty-second embodiment, wherein a quadrupole electrostatic excitation is added to the pair of octupole electrodes to correct for astigmatism.

A sixty-fifth embodiment, which is the x-ray projection system of the sixty-second embodiment, wherein a cubically varying electrostatic excitation is added to the pair of octupole electrodes to correct for distortion.

A sixty-sixth embodiment, which is the x-ray projection system of any of the fifty-first through sixty-fifth embodiments, further including a scanning electron microscope (SEM) column having an optical axis that is substantially aligned with the axis of the planar x-ray target, the sample holder and the planar x-ray detector.

A sixty-seventh embodiment, which is the x-ray projection system of any of the fifty-first through sixty-sixth embodiments, wherein the planar x-ray target comprises a high aspect ratio structure made from a hard x-ray producing material.

A sixty-eighth embodiment, which is the x-ray projection system of any of the fifty-first through sixty-seventh embodiments, The x-ray projection system of claim 67, wherein the high aspect ratio structure is embedded in or formed on a thinned portion of the substrate.

A preferred method or apparatus of the present invention has many novel aspects, and because the invention can be embodied in different methods or apparatuses for different purposes, not every aspect need be present in every embodiment. Moreover, many of the aspects of the described embodiments may be separately patentable. The invention has broad applicability and can provide many benefits as described and shown in the examples above. The embodiments will vary greatly depending upon the specific application, and not every embodiment will provide all of the benefits and meet all of the objectives that are achievable by the invention.

It should be recognized that embodiments of the present invention can be implemented via computer hardware, a combination of both hardware and software, or by computer instructions stored in a non-transitory computer-readable memory. The methods can be implemented in computer programs using standard programming techniques—including a non-transitory computer-readable storage medium configured with a computer program, where the storage medium so configured causes a computer to operate in a specific and predefined manner—according to the methods and figures described in this Specification. Each program may be implemented in a high level procedural or object oriented programming language to communicate with a computer system. However, the programs can be implemented in assembly or machine language, if desired. In any case, the language can be a compiled or interpreted language. Moreover, the program can run on dedicated integrated circuits programmed for that purpose.

Further, methodologies may be implemented in any type of computing platform, including but not limited to, personal computers, mini-computers, main-frames, workstations, networked or distributed computing environments, computer platforms separate, integral to, or in communication with charged particle tools or other imaging devices, and the like. Aspects of the present invention may be implemented in machine readable code stored on a non-transitory storage medium or device, whether removable or integral to the computing platform, such as a hard disc, optical read and/or write storage mediums, RAM, ROM, and the like, so that it is readable by a programmable computer, for configuring and operating the computer when the storage media or device is read by the computer to perform the procedures described herein. Moreover, machine-readable code, or portions thereof, may be transmitted over a wired or wireless network. The invention described herein includes these and other various types of non-transitory computer-readable storage media when such media contain instructions or programs for implementing the steps described above in conjunction with a microprocessor or other data processor. The invention also includes the computer itself when programmed according to the methods and techniques described herein.

Computer programs can be applied to input data to perform the functions described herein and thereby transform the input data to generate output data. The output information is applied to one or more output devices such as a display monitor. In preferred embodiments of the present invention, the transformed data represents physical and tangible objects, including producing a particular visual depiction of the physical and tangible objects on a display.

In the discussion above and in the claims, the terms "including" and "comprising" are used in an open-ended fashion, and thus should be interpreted to mean "including, but not limited to . . . ." To the extent that any term is not specially defined in this specification, the intent is that the term is to be given its plain and ordinary meaning. The accompanying drawings are intended to aid in understanding the present invention and, unless otherwise indicated, are not drawn to scale. Particle beam systems suitable for carrying out the present invention are commercially available, for example, from FEI Company, the assignee of the present application.

Although the present invention and its advantages have been described in detail, it should be understood that various changes, substitutions and alterations can be made to the embodiments described herein without departing from the scope of the invention as defined by the appended claims. Moreover, the scope of the present application is not intended to be limited to the particular embodiments of the process, machine, manufacture, composition of matter, means, methods and steps described in the specification.

For example, while the methods and apparatus disclosed herein have been described for use in an x-ray tomography system, the methods and apparatus can be generally employed in any type of x-ray projection imaging system. Moreover, in addition to obtaining x-ray absorption images, the disclosed methods and apparatus can be used to obtain other types of sample contrast images, such as phase contrast or diffraction contrast images. Phase and diffraction contrast images may be more useful when imaging samples containing small structures. While the SEM minicolumn 1100 (FIG. 11) may be used as the SEM column 260 (FIG. 2), the SEM column 260 may be any convention SEM column or minicolumn. Moreover, rather than employing a single SEM column 260 to image both the target 210 and the sample 220, separate SEM columns can be employed to image each. While the plurality of high aspect ratio structures are described as preferably forming an N×M grid, the grid can be either 1 dimensional or 2 dimensional. Moreover, while the grid elements may preferably appear in a regular and repeating pattern, the grid elements may also appear in an irregular or non-repeating pattern. The x-ray detector 230 shown in FIG. 2 can be constructed to have high sensitivity to the hard x-rays produced by the high aspect ratio structures 212 and low sensitivities to soft x-rays produced by the structures 212 and/or by the substrate on or in which the structures 212 are made. Alternatively, a filter (not shown) can be placed between the x-ray target 210 and the x-ray detector 230 to filter out soft x-rays.

As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

We claim as follows:

1. A method for generating an x-ray image of a sample, comprising:
   sequentially focusing an electron beam on each of a plurality of orthogonal Hadamard matrix structures, each orthogonal Hadamard matrix structure made from a plurality of high aspect ratio structures arranged at different pixel locations in a pixilated grid pattern, each high aspect ratio structure made from a hard x-ray producing material;
   illuminating the sample with x-rays produced by sequentially focusing the electron beam on each of the plurality of orthogonal Hadamard matrix structures;
   sequentially detecting the x-rays transmitted through the sample, and recording the detected x-rays in a plurality of Hadamard transformed x-ray images;
   applying one or more inverse Hadamard transforms to the plurality of Hadamard transformed x-ray images to generate one or more x-ray images, wherein each of the one or more x-ray images is generated from an inverse Hadamard transform corresponding to a different pixel in the pixilated grid of high aspect ratio structures that make up the orthogonal Hadamard matrix structures; and
   combining the one or more x-ray images to generate an x-ray image of the sample.

2. The method of claim 1, wherein each of the orthogonal Hadamard matrix structures is located at a different location on the same x-ray target.

3. The method of claim 2, further comprising determining the location of each of the plurality of orthogonal Hadamard matrix structures on the x-ray target before sequentially focusing the electron beam on each of the plurality of orthogonal Hadamard matrix structures.

4. The method of claim 2, wherein applying the one or more inverse Hadamard transforms includes correcting for relative parallax in each of the Hadamard transformed x-ray images due to the different locations of the orthogonal Hadamard matrix structures on the x-ray target.

5. The method of claim 4, wherein combining the x-ray images includes correcting for relative parallax in each of the x-ray images due to the different pixel locations of the high aspect ratio structures in each of the orthogonal Hadamard matrix structures.

6. The method of claim 1, wherein at least two high aspect ratio structures in each of the plurality of orthogonal Hadamard matrix structures are made from different hard x-ray producing materials, such that the spatial distribution of the at least two high aspect ratio structures made from the different hard x-ray producing materials is the same in each of the plurality of orthogonal Hadamard matrix structures.

7. The method of claim 6, wherein combining the one or more x-ray images includes combining x-ray images corresponding to pixels in the orthogonal Hadamard matrix structures having high aspect ratio structures made from the same hard x-ray producing material.

8. The method of claim 1, wherein applying one or more inverse Hadamard transforms to the plurality of Hadamard transformed x-ray images to generate one or more x-ray images comprises adding or subtracting the plurality of Hadamard transformed x-ray images based on a Hadamard code.

9. The method of claim 1, wherein the plurality of orthogonal Hadamard matrix structures are made from a plurality of high aspect ratio structures made from a first hard x-ray producing material, further comprising:
   sequentially focusing the electron beam on each of a second plurality of orthogonal Hadamard matrix structures, each made from a plurality of high aspect ratio structures made from a second hard x-ray producing material;
   illuminating the sample with the x-rays produced by sequentially focusing the electron beam on each of the second plurality of orthogonal Hadamard matrix structures;
   sequentially detecting the x-rays transmitted through the sample, and recording the detected x-rays in a second plurality of Hadamard transformed x-ray images;
   applying one or more inverse Hadamard transforms to the second plurality of Hadamard transformed x-ray images to generate one or more x-ray images for the second hard x-ray producing material, wherein each of the one or more x-ray images for the second hard x-ray producing material is generated from an inverse Hadamard transform corresponding to a different pixel; and
   combining the one or more x-ray images for the second hard x-ray producing material to generate an x-ray image of the sample for the second hard x-ray producing material.

10. The method of claim 1, wherein the plurality of orthogonal Hadamard matrix structures are made from a plurality of high aspect ratio structures having a first cross sectional area, further comprising:

sequentially focusing the electron beam on each of a second plurality of orthogonal Hadamard matrix structures, each made from a plurality of high aspect ratio structures having a second cross-sectional area;

illuminating the sample with the x-rays produced by sequentially focusing the electron beam on each of the second plurality of orthogonal Hadamard matrix structures;

sequentially detecting the x-rays transmitted through the sample, and recording the detected x-rays in a second plurality of Hadamard transformed x-ray images;

applying one or more inverse Hadamard transforms to the second plurality of Hadamard transformed x-ray images to generate one or more higher resolution x-ray images, wherein each of the one or more higher resolution x-ray images is generated from an inverse Hadamard transform corresponding to a different pixel; and combining the one or more higher resolution x-ray images to generate a higher resolution x-ray image of the sample.

11. A computer program product, embedded on a non-transitory medium, comprising instructions operable to cause a programmable processor to:

sequentially focus an electron beam on each of a plurality of orthogonal Hadamard matrix structures, each Hadamard matrix structure made from a plurality of high aspect ratio structures arranged at different pixel locations in a pixilated grid pattern, each high aspect ratio structure made from a hard x-ray producing material;

sequentially detect x-rays produced by the plurality of orthogonal Hadamard matrix structures and transmitted through a sample, and record the detected x-rays in a plurality of Hadamard transformed x-ray images;

apply one or more inverse Hadamard transforms to the plurality of Hadamard transformed x-ray images to generate one or more x-ray images, wherein each of the one or more x-ray images is generated from an inverse Hadamard transform corresponding to a different pixel in the pixilated grid of high aspect ratio structures that make up the orthogonal Hadamard matrix structures; and combine the one or more x-ray images to generate an x-ray image of the sample.

* * * * *